(12) United States Patent
Wixey et al.

(10) Patent No.: US 11,806,015 B2
(45) Date of Patent: Nov. 7, 2023

(54) SURGICAL INSTRUMENTS HAVING MECHANISMS FOR IDENTIFYING AND/OR DEACTIVATING STAPLER CARTRIDGES

(71) Applicant: INTUITIVE SURGICAL OPERATIONS, INC., Sunnyvale, CA (US)

(72) Inventors: Matthew Wixey, San Jose, CA (US); Atal Patel, Mission Viejo, CA (US); Babak D. Jasemian, Trabuco Canyon, CA (US); Nicholas Ragosta, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 251 days.

(21) Appl. No.: 17/414,819

(22) PCT Filed: Dec. 16, 2019

(86) PCT No.: PCT/US2019/066530
§ 371 (c)(1),
(2) Date: Jun. 16, 2021

(87) PCT Pub. No.: WO2020/131692
PCT Pub. Date: Jun. 25, 2020

(65) Prior Publication Data
US 2022/0015763 A1 Jan. 20, 2022

Related U.S. Application Data

(60) Provisional application No. 62/783,429, filed on Dec. 21, 2018.

(51) Int. Cl.
*A61B 17/072* (2006.01)
*A61B 34/30* (2016.01)
(Continued)

(52) U.S. Cl.
CPC ........ *A61B 17/07207* (2013.01); *A61B 34/30* (2016.02); *A61B 90/08* (2016.02);
(Continued)

(58) Field of Classification Search
CPC .... A61B 17/07207; A61B 2017/07271; A61B 2017/07278; A61B 2017/07285;
(Continued)

(56) References Cited

U.S. PATENT DOCUMENTS 4,305,539 A 12/1981 Korolkov et al.
4,319,576 A 3/1982 Rothfuss
(Continued)

FOREIGN PATENT DOCUMENTS

EP 0277532 B1 8/1990
EP 0277529 B1 4/1993
(Continued)

OTHER PUBLICATIONS

International Search Report and Written Opinion for Application No. PCT/US2020/054568, dated Jan. 29, 2021, 13 pages.
(Continued)

*Primary Examiner* — Valentin Neacsu
(74) *Attorney, Agent, or Firm* — Farber LLC

(57) ABSTRACT

Surgical stapling instruments include mechanisms for identifying and/or deactivating stapler cartridges for use with the instruments. The stapling instrument includes a drive member for actuating a staple cartridge and a locking member movable from a disabled position permitting distal translation of the drive member through a staple firing stroke, to a locking position inhibiting distal translation of the drive member through the staple firing stroke. The staple cartridge may include a switch movable in a lateral direction to either maintain the locking member in the disabled position or to allow the locking member to move into the locking position.

(Continued)

The instrument may further include a stapler cartridge including an annular pin configured to be engaged by a drive member at a an axial position to create a detectable resistance for reload detection by a control unit to identify the type of stapler cartridge present in the surgical stapling instrument.

19 Claims, 31 Drawing Sheets

(51) Int. Cl.
*A61B 90/00* (2016.01)
*A61B 90/90* (2016.01)
*A61B 17/00* (2006.01)

(52) U.S. Cl.
CPC .... *A61B 90/90* (2016.02); *A61B 2017/00017* (2013.01); *A61B 2017/00039* (2013.01); *A61B 2017/07271* (2013.01); *A61B 2017/07278* (2013.01); *A61B 2017/07285* (2013.01); *A61B 2090/0814* (2016.02)

(58) Field of Classification Search
CPC .... A61B 2090/0814; A61B 2090/0801; A61B 2090/08021
USPC ........................................................ 227/175.4
See application file for complete search history.

(56) References Cited

U.S. PATENT DOCUMENTS

| | | |
|---|---|---|
| 4,407,286 A | 10/1983 | Noiles et al. |
| 4,429,695 A | 2/1984 | Green |
| 4,509,518 A | 4/1985 | McGarry et al. |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,767,044 A | 8/1988 | Green |
| 4,809,695 A | 3/1989 | Gwathmey et al. |
| 4,848,637 A | 7/1989 | Pruitt |
| 4,892,244 A | 1/1990 | Fox et al. |
| 4,930,503 A | 6/1990 | Pruitt |
| 4,978,049 A | 12/1990 | Green |
| 5,027,834 A | 7/1991 | Pruitt |
| 5,040,715 A | 8/1991 | Green et al. |
| 5,133,735 A | 7/1992 | Slater et al. |
| 5,133,736 A | 7/1992 | Bales, Jr. et al. |
| 5,147,357 A | 9/1992 | Rose et al. |
| 5,180,092 A | 1/1993 | Crainich |
| 5,275,323 A | 1/1994 | Schulze et al. |
| 5,307,976 A | 5/1994 | Olson et al. |
| 5,312,023 A | 5/1994 | Green et al. |
| 5,334,183 A | 8/1994 | Wuchinich |
| 5,342,395 A | 8/1994 | Jarrett et al. |
| 5,342,396 A | 8/1994 | Cook |
| 5,366,133 A | 11/1994 | Geiste |
| 5,452,836 A | 9/1995 | Huitema et al. |
| 5,452,837 A | 9/1995 | Williamson, IV et al. |
| 5,480,089 A | 1/1996 | Blewett |
| 5,484,095 A | 1/1996 | Green et al. |
| 5,484,451 A | 1/1996 | Akopov et al. |
| 5,487,500 A | 1/1996 | Knodel et al. |
| 5,497,931 A | 3/1996 | Nakamura |
| 5,533,521 A | 7/1996 | Granger |
| 5,540,375 A | 7/1996 | Bolanos et al. |
| 5,554,164 A | 9/1996 | Wilson et al. |
| 5,560,530 A | 10/1996 | Bolanos et al. |
| 5,562,239 A | 10/1996 | Boiarski et al. |
| 5,564,615 A | 10/1996 | Bishop et al. |
| 5,571,116 A | 11/1996 | Bolanos et al. |
| 5,571,285 A | 11/1996 | Chow et al. |
| 5,573,534 A | 11/1996 | Stone |
| 5,615,820 A | 4/1997 | Viola |
| 5,624,452 A | 4/1997 | Yates |
| 5,628,446 A | 5/1997 | Geiste et al. |
| 5,651,491 A | 7/1997 | Heaton et al. |
| 5,652,849 A | 7/1997 | Conway et al. |
| 5,667,626 A | 9/1997 | Cayford et al. |
| 5,673,842 A | 10/1997 | Bittner et al. |
| 5,676,674 A | 10/1997 | Bolanos et al. |
| 5,688,269 A | 11/1997 | Newton et al. |
| 5,690,269 A | 11/1997 | Bolanos et al. |
| 5,693,042 A | 12/1997 | Boiarski et al. |
| 5,697,542 A | 12/1997 | Knodel et al. |
| 5,700,270 A | 12/1997 | Peyser et al. |
| 5,700,276 A | 12/1997 | Benecke |
| 5,709,680 A | 1/1998 | Yates et al. |
| 5,752,644 A | 5/1998 | Bolanos et al. |
| 5,752,973 A | 5/1998 | Kieturakis et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,792,135 A | 8/1998 | Madhani et al. |
| 5,820,009 A | 10/1998 | Melling et al. |
| 5,826,776 A | 10/1998 | Schulze et al. |
| 5,833,695 A | 11/1998 | Yoon |
| 5,865,361 A | 2/1999 | Milliman et al. |
| 5,871,135 A | 2/1999 | Williamson, IV et al. |
| 5,911,353 A | 6/1999 | Bolanos et al. |
| 5,915,616 A | 6/1999 | Viola et al. |
| 5,941,442 A | 8/1999 | Geiste et al. |
| 5,954,259 A | 9/1999 | Viola et al. |
| 5,959,892 A | 9/1999 | Lin et al. |
| 6,032,849 A | 3/2000 | Mastri et al. |
| 6,079,606 A | 6/2000 | Milliman et al. |
| 6,174,309 B1 | 1/2001 | Wrublewski et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,330,956 B1 | 12/2001 | Willinger |
| 6,330,965 B1 | 12/2001 | Milliman et al. |
| 6,488,196 B1 | 12/2002 | Fenton, Jr. |
| 6,503,259 B2 | 1/2003 | Huxel et al. |
| 6,585,735 B1 | 7/2003 | Frazier et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,786,382 B1 | 9/2004 | Hoffman |
| 6,817,974 B2 | 11/2004 | Cooper et al. |
| 6,877,647 B2 | 4/2005 | Green et al. |
| 6,905,057 B2 | 6/2005 | Swayze et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,114,642 B2 | 10/2006 | Whitman |
| 7,128,253 B2 | 10/2006 | Mastri et al. |
| 7,140,527 B2 | 11/2006 | Ehrenfels et al. |
| 7,140,528 B2 | 11/2006 | Shelton, IV et al. |
| 7,258,262 B2 | 8/2007 | Mastri et al. |
| 7,308,998 B2 | 12/2007 | Mastri et al. |
| 7,328,828 B2 | 2/2008 | Ortiz et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,401,721 B2 | 7/2008 | Holsten et al. |
| 7,407,075 B2 | 8/2008 | Holsten et al. |
| 7,455,676 B2 | 11/2008 | Holsten et al. |
| 7,472,814 B2 | 1/2009 | Mastri et al. |
| 7,481,349 B2 | 1/2009 | Holsten et al. |
| 7,494,039 B2 | 2/2009 | Racenet et al. |

(56) References Cited

U.S. PATENT DOCUMENTS

| | | |
|---|---|---|
| 7,565,993 B2 | 7/2009 | Milliman et al. |
| 7,588,174 B2 | 9/2009 | Holsten et al. |
| 7,654,431 B2 | 2/2010 | Hueil et al. |
| 7,658,312 B2 | 2/2010 | Vidal et al. |
| 7,673,783 B2 | 3/2010 | Morgan et al. |
| 7,699,835 B2 | 4/2010 | Lee et al. |
| 7,721,930 B2 | 5/2010 | McKenna et al. |
| 7,726,539 B2 | 6/2010 | Holsten et al. |
| 7,770,774 B2 | 8/2010 | Mastri et al. |
| 7,794,475 B2 | 9/2010 | Hess et al. |
| 7,832,611 B2 | 11/2010 | Boyden et al. |
| 7,837,079 B2 | 11/2010 | Holsten et al. |
| 7,866,526 B2 | 1/2011 | Green et al. |
| 7,942,303 B2 | 5/2011 | Shah et al. |
| 7,950,561 B2 | 5/2011 | Aranyi |
| 8,070,035 B2 | 12/2011 | Holsten et al. |
| 8,083,118 B2 | 12/2011 | Milliman et al. |
| 8,127,975 B2 | 3/2012 | Olson et al. |
| 8,157,152 B2 | 4/2012 | Holsten et al. |
| 8,272,553 B2 | 9/2012 | Mastri et al. |
| 8,308,042 B2 | 11/2012 | Aranyi |
| 8,348,127 B2 | 1/2013 | Marczyk |
| 8,365,972 B2 | 2/2013 | Aranyi et al. |
| 8,371,492 B2 | 2/2013 | Aranyi et al. |
| 8,551,091 B2 | 10/2013 | Couture et al. |
| 8,573,465 B2 | 11/2013 | Shelton, IV |
| 8,579,178 B2 | 11/2013 | Holsten et al. |
| 8,608,047 B2 | 12/2013 | Holsten et al. |
| 8,672,939 B2 | 3/2014 | Garrison |
| 8,783,541 B2 | 7/2014 | Shelton, IV et al. |
| 8,800,841 B2 | 8/2014 | Ellerhorst et al. |
| 8,858,547 B2 | 10/2014 | Brogna |
| 8,864,010 B2 | 10/2014 | Williams |
| 8,905,287 B2 | 12/2014 | Racenet et al. |
| 8,925,785 B2 | 1/2015 | Holsten et al. |
| 9,010,606 B2 | 4/2015 | Aranyi et al. |
| 9,055,961 B2 | 6/2015 | Manzo et al. |
| 9,192,378 B2 | 11/2015 | Aranyi et al. |
| 9,192,379 B2 | 11/2015 | Aranyi et al. |
| 9,211,120 B2 | 12/2015 | Scheib et al. |
| 9,216,019 B2 | 12/2015 | Schmid et al. |
| 9,345,479 B2 | 5/2016 | Racenet et al. |
| 9,717,497 B2 | 8/2017 | Zerkle et al. |
| 9,717,498 B2 | 8/2017 | Aranyi et al. |
| 9,936,949 B2 | 4/2018 | Measamer et al. |
| 10,111,659 B2 | 10/2018 | Racenet et al. |
| 10,130,367 B2 | 11/2018 | Cappola et al. |
| 10,231,732 B1 | 3/2019 | Racenet et al. |
| 10,285,693 B2 | 5/2019 | Kimsey et al. |
| 10,646,219 B2 | 5/2020 | Racenet et al. |
| 10,828,027 B2 | 11/2020 | Racenet et al. |
| 10,863,988 B2 | 12/2020 | Patel et al. |
| 11,234,700 B2 | 2/2022 | Ragosta et al. |
| 11,439,390 B2 | 9/2022 | Patel et al. |
| 11,504,124 B2 | 11/2022 | Patel et al. |
| 11,517,312 B2 | 12/2022 | Wixey |
| 2002/0165562 A1 | 11/2002 | Grant et al. |
| 2003/0135204 A1 | 7/2003 | Lee et al. |
| 2003/0181910 A1 | 9/2003 | Dycus et al. |
| 2004/0232199 A1 | 11/2004 | Shelton et al. |
| 2004/0267310 A1 | 12/2004 | Racenet et al. |
| 2005/0006430 A1 | 1/2005 | Wales |
| 2005/0006434 A1 | 1/2005 | Wales et al. |
| 2005/0070925 A1 | 3/2005 | Shelton, IV et al. |
| 2005/0070958 A1 | 3/2005 | Swayze et al. |
| 2005/0101991 A1 | 5/2005 | Ahlberg et al. |
| 2005/0113826 A1 | 5/2005 | Johnson et al. |
| 2005/0178813 A1 | 8/2005 | Swayze et al. |
| 2005/0187576 A1 | 8/2005 | Whitman et al. |
| 2005/0273084 A1 | 12/2005 | Hinman et al. |
| 2005/0273085 A1 | 12/2005 | Hinman et al. |
| 2006/0000868 A1 | 1/2006 | Shelton, IV et al. |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |
| 2006/0024817 A1 | 2/2006 | Deguchi et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton, IV |
| 2006/0049230 A1 | 3/2006 | Shelton, IV et al. |
| 2006/0097026 A1 | 5/2006 | Shelton, IV |
| 2006/0111209 A1 | 5/2006 | Hinman et al. |
| 2006/0111210 A1 | 5/2006 | Hinman |
| 2006/0161190 A1 | 7/2006 | Gadberry et al. |
| 2006/0190031 A1 | 8/2006 | Wales et al. |
| 2006/0226196 A1 | 10/2006 | Hueil et al. |
| 2007/0010838 A1 | 1/2007 | Shelton, IV et al. |
| 2007/0045379 A1 | 3/2007 | Shelton, IV |
| 2007/0250113 A1 | 10/2007 | Hegeman et al. |
| 2007/0262116 A1 | 11/2007 | Hueil et al. |
| 2008/0023522 A1 | 1/2008 | Olson et al. |
| 2008/0078804 A1 | 4/2008 | Shelton et al. |
| 2008/0086114 A1 | 4/2008 | Schmitz et al. |
| 2009/0277947 A1 | 11/2009 | Viola |
| 2010/0006620 A1 | 1/2010 | Sorrentino et al. |
| 2010/0076474 A1 | 3/2010 | Yates et al. |
| 2010/0108740 A1 | 5/2010 | Pastorelli et al. |
| 2010/0145334 A1 | 6/2010 | Olson et al. |
| 2010/0179545 A1 | 7/2010 | Twomey et al. |
| 2010/0198248 A1 | 8/2010 | Vakharia |
| 2010/0331857 A1 | 12/2010 | Doyle et al. |
| 2011/0022078 A1 | 1/2011 | Hinman |
| 2011/0118707 A1 | 5/2011 | Burbank |
| 2011/0152879 A1 | 6/2011 | Williams |
| 2011/0174863 A1 | 7/2011 | Shelton, IV et al. |
| 2011/0251612 A1 | 10/2011 | Faller et al. |
| 2011/0251613 A1 | 10/2011 | Guerra et al. |
| 2011/0290851 A1 | 12/2011 | Shelton, IV |
| 2011/0290854 A1 | 12/2011 | Timm et al. |
| 2011/0295270 A1 | 12/2011 | Giordano et al. |
| 2011/0301603 A1 | 12/2011 | Kerr et al. |
| 2012/0000962 A1 | 1/2012 | Racenet et al. |
| 2012/0022584 A1 | 1/2012 | Donnigan et al. |
| 2012/0071891 A1 | 3/2012 | Itkowitz et al. |
| 2012/0223121 A1 | 9/2012 | Viola et al. |
| 2012/0228358 A1* | 9/2012 | Zemlok ............ A61B 17/07207 227/176.1 |
| 2012/0248167 A1* | 10/2012 | Flanagan ............ A61B 17/072 227/2 |
| 2012/0255986 A1 | 10/2012 | Petty et al. |
| 2013/0015231 A1 | 1/2013 | Kostrzewski |
| 2013/0046303 A1 | 2/2013 | Evans et al. |
| 2013/0056521 A1 | 3/2013 | Swensgard |
| 2013/0068821 A1 | 3/2013 | Huitema et al. |
| 2013/0087599 A1 | 4/2013 | Krumanaker et al. |
| 2013/0098965 A1* | 4/2013 | Kostrzewski ........ A61B 17/072 227/176.1 |
| 2013/0126586 A1 | 5/2013 | Zhang et al. |
| 2013/0148577 A1 | 6/2013 | Terry et al. |
| 2013/0248577 A1 | 9/2013 | Leimbach et al. |
| 2013/0277410 A1 | 10/2013 | Fernandez et al. |
| 2013/0296922 A1 | 11/2013 | Allen, IV et al. |
| 2013/0327808 A1 | 12/2013 | Chen et al. |
| 2014/0001236 A1 | 1/2014 | Shelton, IV et al. |
| 2014/0005653 A1 | 1/2014 | Shelton, IV et al. |
| 2014/0021239 A1 | 1/2014 | Kostrzewski |
| 2014/0025071 A1 | 1/2014 | Sims et al. |
| 2014/0100600 A1 | 4/2014 | Kendrick |
| 2014/0175152 A1 | 6/2014 | Hess et al. |
| 2014/0180286 A1 | 6/2014 | Marczyk et al. |
| 2014/0200596 A1 | 7/2014 | Weir et al. |
| 2014/0214049 A1 | 7/2014 | Jeong et al. |
| 2014/0257331 A1 | 9/2014 | Kim et al. |
| 2014/0263546 A1 | 9/2014 | Aranyi |
| 2014/0263559 A1 | 9/2014 | Williams et al. |
| 2014/0263567 A1 | 9/2014 | Williams et al. |
| 2014/0263569 A1 | 9/2014 | Williams et al. |
| 2014/0284372 A1 | 9/2014 | Kostrzewski |
| 2014/0343550 A1 | 11/2014 | Faller et al. |
| 2014/0343569 A1 | 11/2014 | Turner |
| 2014/0364851 A1 | 12/2014 | Batross et al. |

(56) References Cited

U.S. PATENT DOCUMENTS

| | | |
|---|---|---|
| 2015/0173789 A1 | 6/2015 | Baxter, III et al. |
| 2015/0209037 A1 | 7/2015 | Kostrzewski et al. |
| 2015/0250530 A1 | 9/2015 | Manzo et al. |
| 2015/0256609 A1 | 9/2015 | Morton et al. |
| 2015/0272575 A1 | 10/2015 | Leimbach et al. |
| 2015/0272576 A1 | 10/2015 | Cappola |
| 2015/0297227 A1 | 10/2015 | Huitema et al. |
| 2015/0297235 A1 | 10/2015 | Harris et al. |
| 2016/0038227 A1 | 2/2016 | Garrison |
| 2016/0058450 A1 | 3/2016 | Shelton, IV et al. |
| 2016/0066916 A1 | 3/2016 | Overmyer et al. |
| 2016/0120544 A1 | 5/2016 | Shelton, IV et al. |
| 2016/0157863 A1 | 6/2016 | Williams et al. |
| 2016/0174977 A1 | 6/2016 | Lytle, IV et al. |
| 2016/0175033 A1 | 6/2016 | Le |
| 2016/0192999 A1 | 7/2016 | Stulen et al. |
| 2016/0235489 A1 | 8/2016 | Gombert et al. |
| 2016/0249921 A1 | 9/2016 | Cappola et al. |
| 2016/0270780 A1 | 9/2016 | Hall et al. |
| 2016/0287251 A1 | 10/2016 | Shelton, IV et al. |
| 2016/0338764 A1 | 11/2016 | Krastins et al. |
| 2017/0010578 A1 | 1/2017 | Miyakawa |
| 2017/0042604 A1 | 2/2017 | McFarland et al. |
| 2017/0079710 A1 | 3/2017 | Deville et al. |
| 2017/0097035 A1 | 4/2017 | Zimmerman et al. |
| 2017/0135746 A1 | 5/2017 | Tetzlaff et al. |
| 2017/0189028 A1 | 7/2017 | Aranyi |
| 2017/0231653 A1 | 8/2017 | Kapadia |
| 2017/0245857 A1 | 8/2017 | Shelton, IV et al. |
| 2017/0290584 A1 | 10/2017 | Jasemian et al. |
| 2017/0296172 A1 | 10/2017 | Harris et al. |
| 2017/0296173 A1 | 10/2017 | Shelton, IV et al. |
| 2018/0008265 A1 | 1/2018 | Hatanaka et al. |
| 2018/0021042 A1 | 1/2018 | Nicholas et al. |
| 2018/0161052 A1 | 6/2018 | Weir et al. |
| 2018/0168581 A1 | 6/2018 | Hunter et al. |
| 2018/0168622 A1 | 6/2018 | Shelton, IV et al. |
| 2018/0168628 A1 | 6/2018 | Hunter et al. |
| 2018/0168637 A1* | 6/2018 | Harris ................... A61B 90/03 |
| 2018/0168641 A1* | 6/2018 | Harris ................... A61B 17/29 |
| 2018/0168642 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0206844 A1 | 7/2018 | Harris et al. |
| 2018/0214200 A1 | 8/2018 | Nanditale et al. |
| 2018/0232951 A1 | 8/2018 | Alterovitz et al. |
| 2018/0296213 A1 | 10/2018 | Strobl |
| 2018/0310948 A1 | 11/2018 | Stamm et al. |
| 2018/0317915 A1 | 11/2018 | McDonald, II |
| 2019/0000454 A1 | 1/2019 | Swayze et al. |
| 2019/0015124 A1 | 1/2019 | Williams et al. |
| 2019/0059894 A1 | 2/2019 | Kumada et al. |
| 2019/0083086 A1 | 3/2019 | Klaffenböck et al. |
| 2019/0099181 A1 | 4/2019 | Shelton, IV et al. |
| 2019/0125347 A1 | 5/2019 | Stokes et al. |
| 2019/0142531 A1 | 5/2019 | Wentworth et al. |
| 2019/0201146 A1 | 7/2019 | Shelton, IV et al. |
| 2019/0231350 A1 | 8/2019 | Scott et al. |
| 2019/0239881 A1 | 8/2019 | Laurent et al. |
| 2019/0290374 A1 | 9/2019 | Ramadorai |
| 2019/0298356 A1 | 10/2019 | Shelton, IV et al. |
| 2019/0314107 A1 | 10/2019 | Worrell et al. |
| 2019/0365458 A1 | 12/2019 | Whitlock et al. |
| 2020/0397430 A1 | 12/2020 | Patel et al. |
| 2021/0000557 A1 | 1/2021 | Mustufa et al. |
| 2021/0022736 A1 | 1/2021 | Wixey |
| 2021/0077101 A1 | 3/2021 | Patel et al. |
| 2021/0177495 A1 | 6/2021 | Ross et al. |
| 2021/0177500 A1 | 6/2021 | Khalaji |
| 2021/0212683 A1 | 7/2021 | Burbank |
| 2021/0267596 A1 | 9/2021 | Fanelli et al. |
| 2021/0386427 A1 | 12/2021 | Millman et al. |
| 2022/0015762 A1* | 1/2022 | Wixey ................... A61B 90/98 |
| 2022/0015763 A1* | 1/2022 | Wixey ................... A61B 34/30 |
| 2022/0015823 A1 | 1/2022 | Wilson et al. |
| 2022/0054130 A1 | 2/2022 | Overmyer et al. |
| 2022/0061836 A1 | 3/2022 | Parihar et al. |
| 2022/0061840 A1 | 3/2022 | Hites |
| 2022/0061841 A1 | 3/2022 | Wixey et al. |
| 2022/0071632 A1 | 3/2022 | Patel et al. |
| 2022/0079585 A1 | 3/2022 | Egan |
| 2022/0125428 A1 | 4/2022 | Ragosta et al. |
| 2022/0160358 A1 | 5/2022 | Wixey |
| 2022/0183686 A1 | 6/2022 | Wixey et al. |
| 2022/0192665 A1 | 6/2022 | Wellman |
| 2022/0346790 A1 | 11/2022 | Wellman |
| 2022/0378537 A1 | 12/2022 | Hites et al. |
| 2022/0395270 A1 | 12/2022 | Patel et al. |

FOREIGN PATENT DOCUMENTS

| | | |
|---|---|---|
| EP | 0641546 A1 | 3/1995 |
| EP | 1090592 A1 | 4/2001 |
| EP | 1728473 A1 | 12/2006 |
| EP | 1479346 B1 | 1/2007 |
| EP | 1621141 B1 | 7/2007 |
| EP | 1316290 B1 | 2/2012 |
| EP | 1754445 B1 | 10/2013 |
| EP | 3135225 A2 | 3/2017 |
| EP | 3158947 A1 | 4/2017 |
| EP | 3173029 A1 | 5/2017 |
| FR | 2828952 B1 | 12/2005 |
| JP | 5301166 B2 | 9/2013 |
| JP | 2014530653 A | 11/2014 |
| JP | 2016508792 A | 3/2016 |
| JP | 2016513570 A | 5/2016 |
| JP | 2017500146 A | 1/2017 |
| JP | 2017513564 A | 6/2017 |
| JP | 2017527396 A | 9/2017 |
| JP | 6411461 B2 | 10/2018 |
| JP | 2019141659 A | 8/2019 |
| SU | 405234 A1 | 9/1975 |
| SU | 886900 A1 | 12/1981 |
| SU | 1333319 A2 | 8/1987 |
| SU | 1442191 A1 | 12/1988 |
| SU | 1459659 A1 | 2/1989 |
| WO | WO-8602254 A1 | 4/1986 |
| WO | WO-9005489 A1 | 5/1990 |
| WO | WO-9734533 A1 | 9/1997 |
| WO | WO-03094743 A1 | 11/2003 |
| WO | WO-03094746 A1 | 11/2003 |
| WO | WO-03094747 A1 | 11/2003 |
| WO | WO-2012142872 A1 | 10/2012 |
| WO | WO-2014106275 A1 | 7/2014 |
| WO | WO-2017026141 A1 | 2/2017 |
| WO | WO-2017034803 A2 | 3/2017 |
| WO | WO-2017156070 A1 | 9/2017 |
| WO | WO-2017214243 A1 | 12/2017 |
| WO | WO-2018005750 A1 | 1/2018 |
| WO | WO-2018071497 A1 | 4/2018 |
| WO | WO-2018118402 A1 | 6/2018 |

OTHER PUBLICATIONS

International Preliminary Report on Patentability for Application No. PCT/US2019/017646, dated Aug. 27, 2020, 10 pages.
International Preliminary Report on Patentability for Application No. PCT/US2019/019501, dated Sep. 3, 2020, 7 pages.
International Search Report and Written Opinion for Application No. PCT/US2020/025655, dated Jul. 22, 2020, 8 pages.
International Search Report and Written Opinion for Application No. PCT/US19/17646, dated Apr. 16, 2019, 11 pages.
International Search Report and Written Opinion for Application No. PCT/US2019/019501, dated May 9, 2019, 8 pages.
International Search Report and Written Opinion for Application No. PCT/US2019/056979, dated Dec. 18, 2019, 8 pages.
International Search Report and Written Opinion for Application No. PCT/US2019/062344, dated Mar. 23, 2020, 17 pages.
International Search Report and Written Opinion for Application No. PCT/US2019/062768, dated Mar. 9, 2020, 15 pages.
International Search Report and Written Opinion for Application No. PCT/US2019/064861, dated Mar. 30, 2020, 18 pages.

(56) References Cited

OTHER PUBLICATIONS

International Search Report and Written Opinion for Application No. PCT/US2019/066513, dated Apr. 21, 2020, 8 pages.
International Search Report and Written Opinion for Application No. PCT/US2019/066530, dated Apr. 21, 2020, 8 pages.
International Search Report and Written Opinion for Application No. PCT/US2020/020672, dated Jun. 29, 2020, 10 pages.
International Search Report and Written Opinion for Application No. PCT/US2020/033481, dated Sep. 3, 2020, 22 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Supplementary European Search Report for Application No. EP19873128.3, dated Jun. 22, 2022, 7 pages.
European Search Report (Corrected version) for Application No. EP19750317.0, dated Mar. 28, 2022, 26 pages.
Partial European Search Report for Application No. EP19757451.0, dated Feb. 2, 2022, 12 pages.
International Search Report and Written Opinion for Application No. PCT/US2021/012284, dated May 6, 2021, 23 pages.

\* cited by examiner

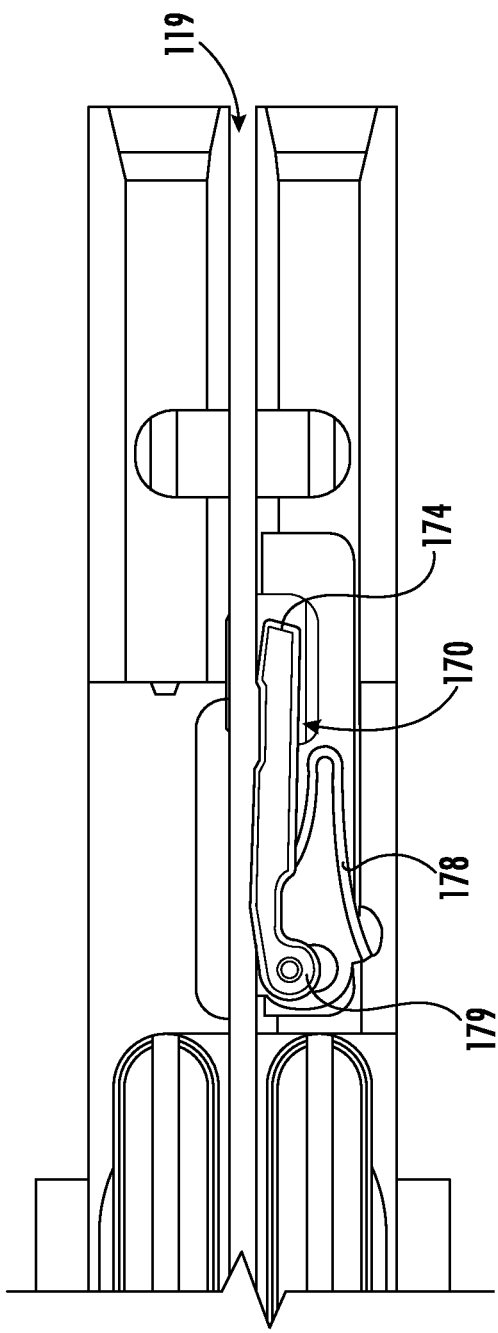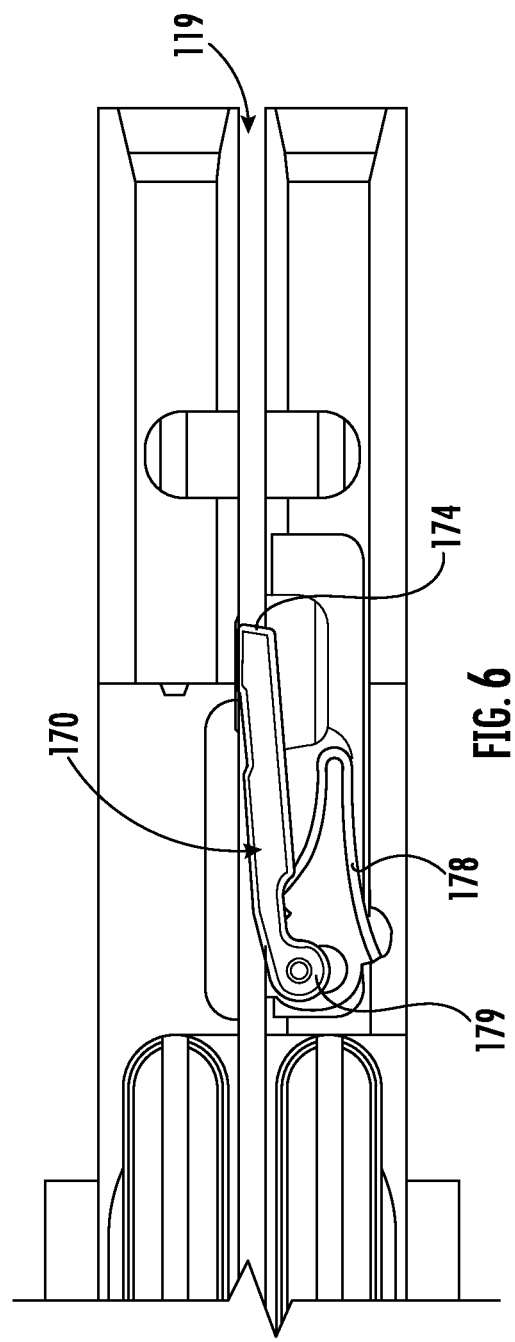

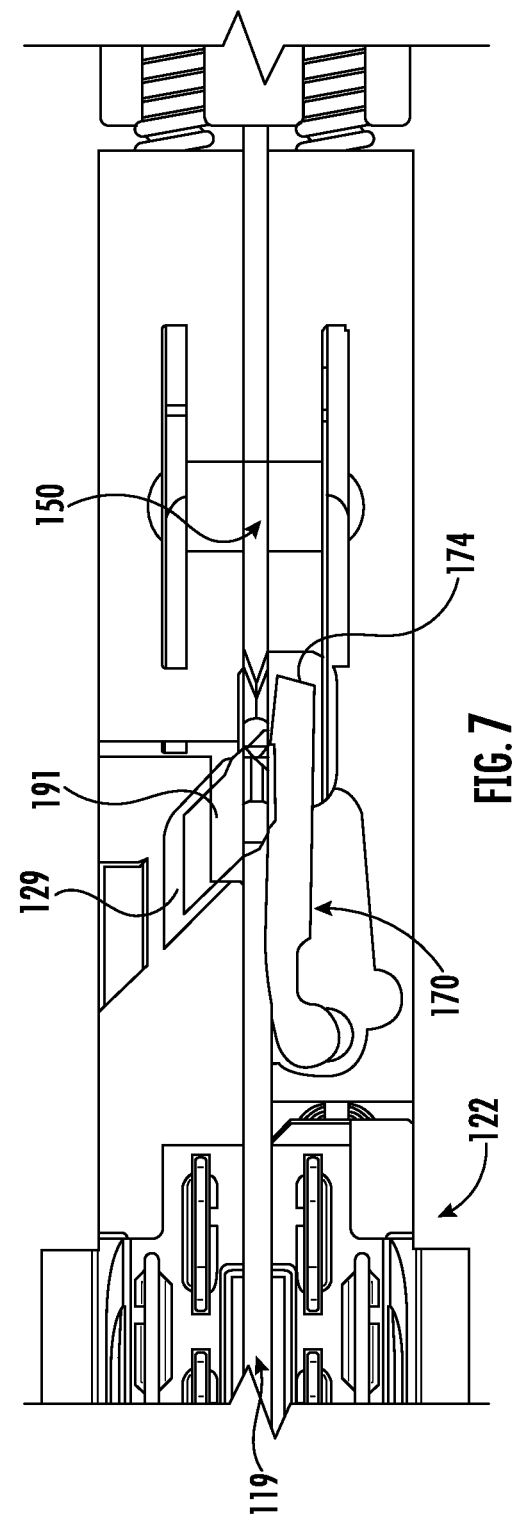

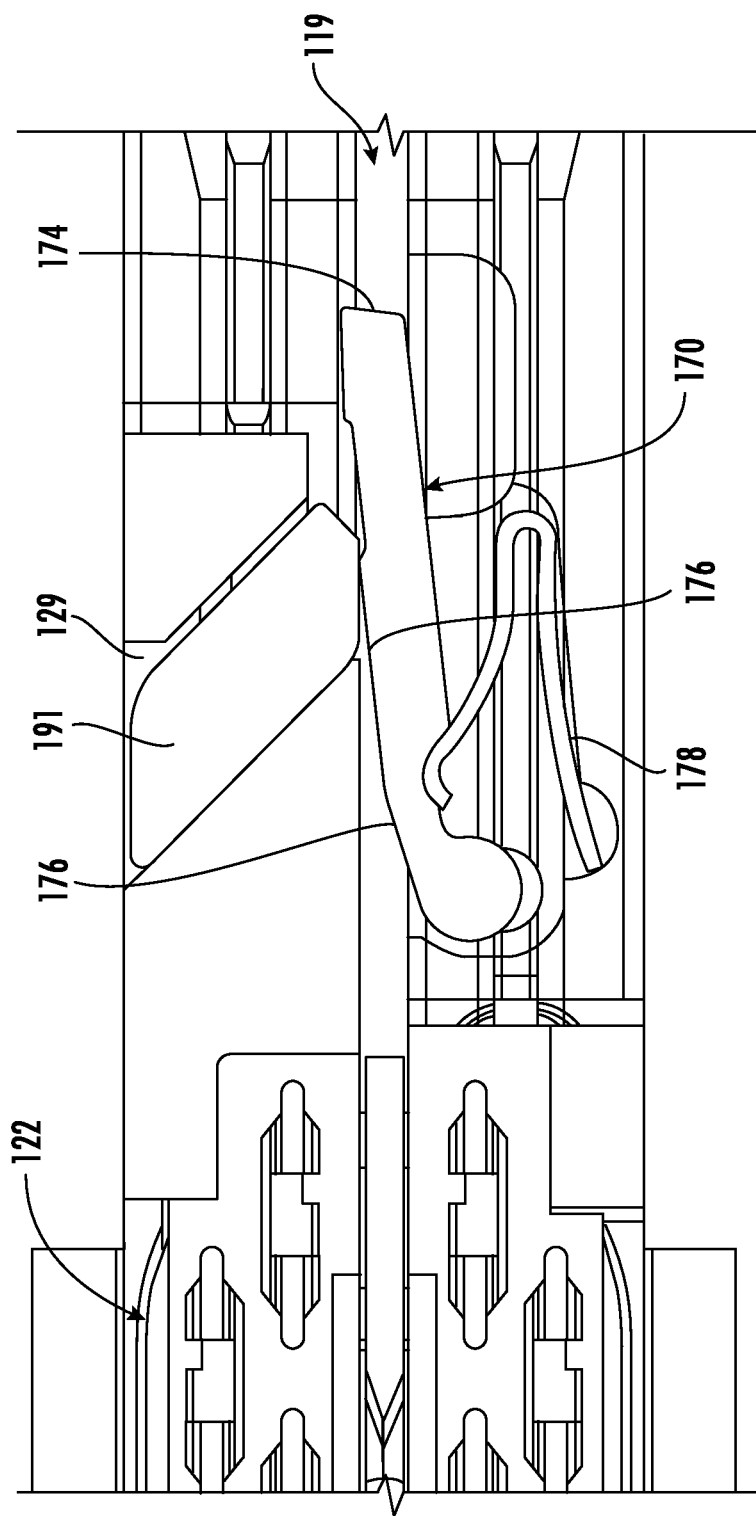

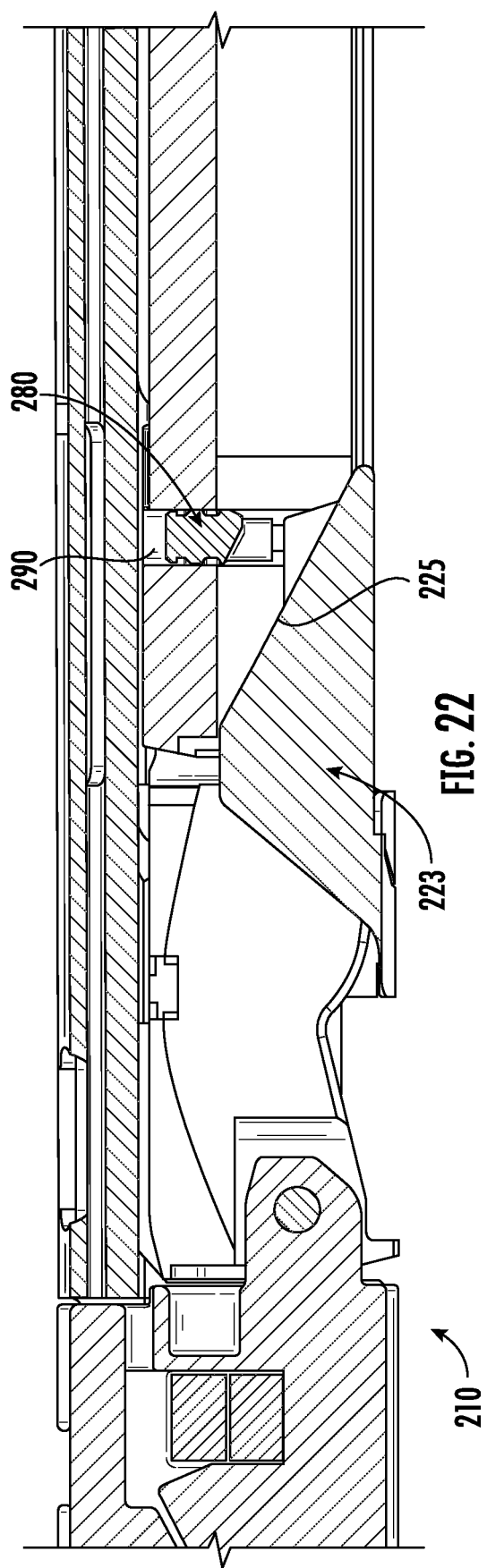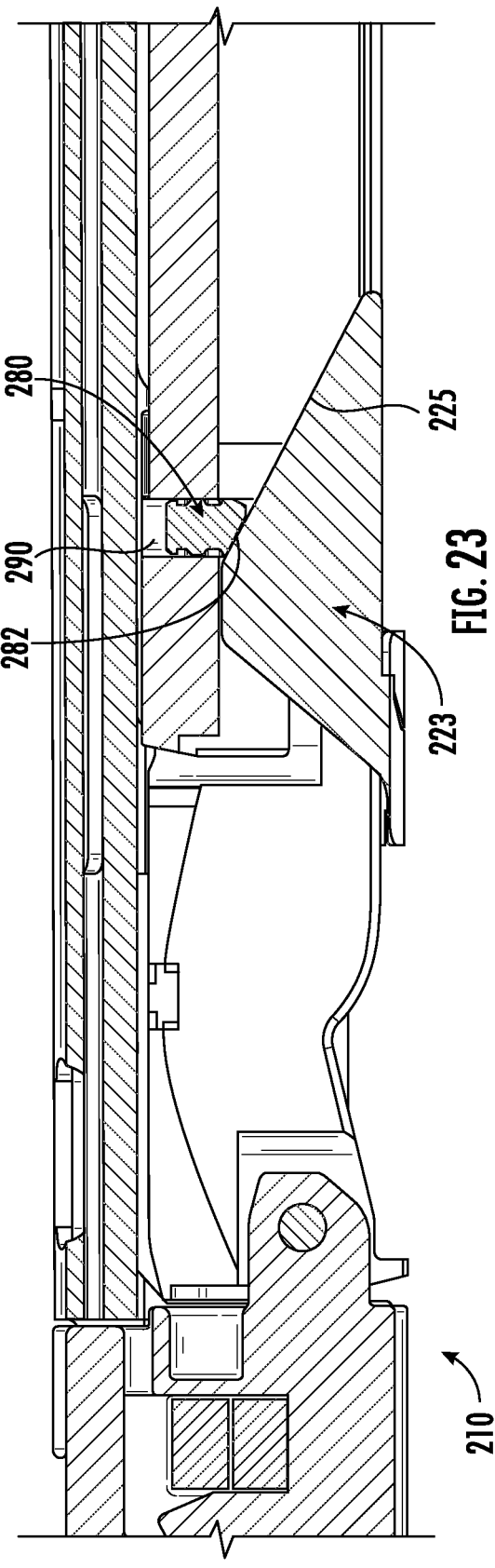

SURGICAL INSTRUMENTS HAVING MECHANISMS FOR IDENTIFYING AND/OR DEACTIVATING STAPLER CARTRIDGES

CROSS REFERENCE TO RELATED APPLICATIONS

This application is the National Stage of International Application No. PCT/US2019/066530 filed Dec. 16, 2019, which claims benefit of U.S. Provisional Application No. 62/783,429, filed Dec. 21, 2018, the entire disclosure of which is incorporated herein by reference for all purposes.

BACKGROUND

The field of the present disclosure relates to medical instruments, and more particularly to tissue sealing instruments for use in surgeries. Even more particularly, the present disclosure relates to a surgical stapling instrument having a novel switch-activated lockout mechanism to prevent firing of a surgical stapling instrument while a spent stapler cartridge remains in place on the jaw. The present disclosure further relates to a surgical stapling instrument including a reload detection mechanism.

Minimally invasive medical techniques are intended to reduce the amount of extraneous tissue that is damaged during diagnostic or surgical procedures, thereby reducing patient, recovery time, discomfort, and deleterious side effects. One effect of minimally invasive surgery, for example, is reduced post-operative hospital recovery times. The average hospital stay for a standard open surgery is typically significantly longer than the average stay for an analogous minimally invasive surgery (MIS). Thus, increased use of MIS could save millions of dollars in hospital costs each year. While many of the surgeries performed each year in the United States could potentially be performed in a minimally invasive manner, only a portion of the current surgeries uses these advantageous techniques due to limitations in minimally invasive surgical instruments and the additional surgical training involved in mastering them.

Improved surgical instruments such as tissue access, navigation, dissection and sealing instruments have enabled MIS to redefine the field of surgery. These instruments allow surgeries and diagnostic procedures to be performed with reduced trauma to the patient. A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console, which in turn control motion of the servo-mechanically operated slave instruments.

The servomechanism used for telesurgery will often accept input from two master controllers (one for each of the surgeon's hands) and may include two or more robotic arms. A surgical instrument is mounted on each of the robotic arms. Operative communication between master controllers and associated robotic arm and instrument assemblies is typically achieved through a control system. The control system typically includes at least one processor that relays input commands from the master controllers to the associated robotic arm and instrument assemblies and back in the case of, for example, force feedback or the like. One example of a robotic surgical system is the DA VINCI™ system commercialized by Intuitive Surgical, Inc. of Sunnyvale, California.

A variety of structural arrangements have been used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912, 6,758,843, 6,246,200, and 5,800,423, the full disclosures of which are incorporated herein by reference in their entirety for all purposes. These linkages often manipulate an instrument holder to which an instrument having a shaft is mounted. Such a manipulator structure can include a parallelogram linkage portion that generates motion of the instrument holder that is limited to rotation about a pitch axis that intersects a remote center of manipulation located along the length of the instrument shaft. Such a manipulator structure can also include a yaw joint that generates motion of the instrument holder that is limited to rotation about a yaw axis that is perpendicular to the pitch axis and that also intersects the remote center of manipulation. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially hazardous forces against the abdominal wall. Alternative manipulator structures are described, for example, in U.S. Pat. Nos. 6,702,805, 6,676,669, 5,855,583, 5,808,665, 5,445,166, and 5,184,601, the full disclosures of which are incorporated herein by reference in their entirety for all purposes.

During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices. Manipulation and control of these end effectors is a particularly beneficial aspect of robotic surgical systems. For this reason, it is desirable to provide surgical tools that include mechanisms that provide two or three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Surgical instruments are often deployed into restrictive body cavities (e.g., through a cannula to inside the pelvis). Accordingly, it is desirable for the surgical instrument to be both compact and maneuverable for best access to and visibility of the surgical site. Known surgical instruments, however, may fail to be both compact and maneuverable. For example, known surgical instruments may lack maneuverability with respect to multiple degrees of freedom (e.g., roll, pitch, and yaw) and associated desired ranges of motion.

Surgical clamping and cutting instruments (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastrointestinal tract. Many known surgical clamping and cutting devices, including known surgical staplers, have opposing jaws that clamp tissue and an articulated knife to cut the clamped tissue.

Many surgical clamping and cutting instruments include an instrument shaft supporting an end effector to which a replaceable stapler cartridge is mounted. An actuation mechanism articulates the stapler cartridge to deploy staples from the stapler cartridge to staple tissue clamped between the stapler cartridge and an articulable jaw of the end effector. Different types of stapler cartridges (or reloads) can be used that have different staple lengths suitable for different tissues to be stapled.

The use of replaceable stapler cartridges does, however, give rise to some additional issues. For example, prior to use, a suitable stapler cartridge having the correct staple length should be mounted to the end effector. If a stapler cartridge having an unsuitable staple length is mistakenly mounted to the end effector, the tissue may be stapled with the unsuitable length staples if the error is not detected and corrected prior to stapling of the tissue. As another example, if a previously used stapler cartridge is not replaced with a suitable new stapler cartridge, the tissue clamped between the previously used stapler cartridge and the articulable jaw cannot be stapled due to the lack of staples to deploy. A similar problem can arise if no stapler cartridge is mounted to the end effector.

The potential disadvantages of firing a surgical stapling instrument while a spent stapler cartridge remains in place on the jaw has given rise to the development of various lockout mechanisms. However, incorporating conventional lockout features typically increases the diameter of the end effector, increasing overall instrument size and making a given instrument less ideal for minimally invasive surgery.

Accordingly, while the new telesurgical systems and devices have proven highly effective and advantageous, still further improvements would be desirable. In general, it would be desirable to have a relatively compact mechanism in place to prevent firing of a surgical stapling instrument while a spent stapler cartridge remains in place on the jaw. In addition, it would be desirable to have a mechanism allowing a robotic or manual surgical system to detect the type of reload installed. Thus, a need exists for a reload detection mechanism that can detect: whether a stapler cartridge is mounted to the surgical instrument; whether the mounted stapler cartridge is unfired (i.e., fresh) or has already been fired; and/or the type of the mounted stapler cartridge mounted to the end effector to ensure that the mounted stapler cartridge has a suitable staple length for the tissue to be stapled.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure relates to surgical stapling instruments that have devices or mechanisms for identifying and/or deactivating disposable stapler cartridges for use with the stapling instruments. The stapling instrument includes a drive member for actuating a staple cartridge and a locking member movable from a disabled position permitting distal translation of the drive member through a staple firing stroke, to a locking position inhibiting distal translation of the drive member through the staple firing stroke. The staple cartridge may include a switch, pin or other mechanism for maintaining the locking member in the disabled position. The switch may be further configured to operate as a reload detection mechanism for determining the type of reload present in the surgical stapling instrument.

In one embodiment, a surgical stapling instrument includes an end effector defining a longitudinal axis including a first jaw and a second jaw. The first jaw includes an anvil and the second jaw is configured to receive a stapler cartridge having one or more staples and a switch movably coupled to the stapler cartridge. The surgical stapling instrument further includes a drive member configured to translate distally and an actuation mechanism configured to translate the drive member distally through the end effector. The surgical stapling instrument further includes a locking member movable from a disabled position permitting distal translation of the drive member to at least an axial position wherein the drive member engages at least one of the staples, to a locking position inhibiting distal translation of the drive member to said axial position. The locking member is configured to move between the disabled and locked positions based on a lateral position of the switch.

One of the advantages of the present disclosure is that the switch can be configured to maintain the locking member in the disabled position and thus allow distal translation of the drive member to actuate the staples when the staple cartridge is fresh (i.e., not having been already fired). On the other hand, the switch can be configured to allow the locking member to move into the locking position during actuation of the staples (i.e., as the drive member is translated distally through the end effector). This effectively locks the instrument such that it cannot actuate a stapler cartridge that has already been fired.

In embodiments, the locking member is movable in a first lateral direction substantially perpendicular to the longitudinal axis from the disabled position to the locking position.

In embodiments, the surgical stapling instrument further includes a stapler cartridge. The switch is positioned within a slot formed on a tail portion of the staple cartridge and is movable is movable in a lateral direction relative the longitudinal axis, from a first position wherein the switch maintains the locking member in the disabled position to a second position wherein the switch disengages the locking member.

One of the advantages of the present disclosure is that, because the switch moves laterally, it may be retained within the end effector of the surgical instrument on a side that is opposite the locking member, such that the switch and the locking member do not have to compete for space within the end effector, allowing for maintenance of reduced instrument size.

In embodiments, locking member is biased towards the locking position.

In embodiments, the locking member includes a switch contacting portion and a proximal engagement portion for obstructing the drive member when the locking member is in the second position. In embodiments, the drive member includes a knife, an inclined surface, and a chamfered surface.

In embodiments, upon distal advancement of the drive member, the chamfered surface of the drive member engages a chamfered surface of the switch while the switch is in the first position.

In embodiments, the slot formed on the tail portion of the cartridge includes series of detents formed therein. The detents are configured to provide mechanical resistance when the drive member engages the switch.

In embodiments, the locking member pivots between the disabled position and the locking position. In embodiments, the locking member pivots about a pivot point that is laterally offset from the longitudinal axis of the end effector. In embodiments, the locking member pivots in a direction substantially perpendicular to the longitudinal axis defined by the end effector.

In embodiments, the actuation mechanism includes a coil that applies a distal force to the first portion of the drive member. In embodiments, the surgical further includes an elongated shaft. The end effector is mounted on a distal end portion of the elongated shaft. In embodiments, the surgical stapling instrument further includes an articulation mechanism configured to articulate the end effector relative to the elongate shaft.

In embodiments, the surgical stapling instrument further includes an actuator operatively connected to the actuation mechanism. In embodiments, the actuator includes a movable handle of a handle assembly provided at the proximal end portion of the surgical instrument. In embodiments, the actuator includes a control device of a robotic surgical system. In embodiments, the drive member includes a knife configured to cut tissue grasped between the first and second jaw.

In another aspect, the present disclosure relates to a surgical stapling instrument including a stapler cartridge having a switch. The surgical stapling instrument further includes an end effector defining a longitudinal axis including a first jaw and a second jaw. The first jaw includes an anvil and, the second jaw is configured to receive the stapler cartridge. The surgical stapling instrument further includes a drive member configured to translate distally through the end effector and an actuation mechanism configured to translate the drive member distally through the end effector. The drive member is configured to contact the switch at an axial position of the drive member relative to the end effector. The switch is configured to provide a detectable resistance upon engagement of the drive member at said axial position. Thus, in accordance with the present disclosure, the detectable resistance may provide input for a reload detection mechanism that can detect: whether a stapler cartridge is mounted to the surgical instrument; whether the mounted stapler cartridge is unfired (or fresh) or has already been fired; and/or the type of the mounted stapler cartridge mounted to the end effector to ensure that the mounted stapler cartridge has a suitable staple length for the tissue to be stapled, based on the detectable resistance.

In embodiments, the switch is positioned within a slot formed on a tail portion of the stapler cartridge. In embodiments, the switch is made of metal.

In embodiments, the drive member includes a knife, an inclined surface, and a chamfered surface. In embodiments, upon distal advancement of the drive member, the chamfered surface of the drive member engages a chamfered surface of the switch.

In embodiments, the surgical instrument is operatively coupled to a surgical system including a control unit. The control unit is configured to process the detectable resistance to identify a type of reload present in the surgical stapling instrument.

In embodiments, the surgical stapling instrument further including a locking member. The switch is movable in a first lateral direction substantially perpendicular to the longitudinal axis, from a first position wherein the switch maintains the locking member in a disabled position to a second position wherein the switch disengages from the locking member.

In embodiments, wherein the slot formed on the tail portion of the cartridge includes series of detents formed therein. The detents are configured to provide mechanical resistance when the drive member engages the switch. In embodiments, the actuation mechanism includes a coil that applies a distal force to the first portion of the drive member. In embodiments, the surgical stapling instrument further includes an elongated shaft, the end effector mounted on a distal end portion of the elongated shaft.

In embodiments, surgical stapling instruments in accordance with this disclosure further include an articulation mechanism configured to articulate the end effector relative to the elongate shaft. In embodiments, surgical stapling instruments further include an actuator operatively connected to the actuation mechanism. In embodiments, the actuator includes a movable handle of a handle assembly provided at the proximal end portion of the surgical instrument. In embodiments, the actuator includes a control device of a robotic surgical system. In embodiments, the drive member includes a knife configured to cut tissue grasped between the first and second jaw.

In other embodiments, the switch comprises an annular pin positioned within a channel formed in the stapler cartridge, the annular pin movable from an unraised position to a second raised position within the channel formed in the stapler cartridge. In embodiments, the channel formed in the staple cartridge includes at least one interference structure formed therein. The at least one interference structure is configured to retain the annular pin within the channel formed in the staple cartridge.

In embodiments, the annular pin includes one or more undercuts formed thereon to engage with the interference structure to retain the annular pin within the channel formed in the staple cartridge.

In embodiments, the surgical instrument is operatively coupled to a surgical system including a control unit, the control unit configured to process the detectable resistance to identify a type of reload present in the surgical stapling instrument.

In yet another aspect, the present disclosure relates to a surgical kit. The surgical kit includes a surgical instrument including an end effector defining a longitudinal axis including a first jaw and a second jaw. The first jaw includes an anvil and, the second jaw is configured to receive a stapler cartridge. The surgical instrument further includes a drive member configured to translate distally through the end effector and an actuation mechanism configured to translate the drive member distally through the end effector. The kit further includes a stapler cartridge including a switch positioned at an axial position on the stapler cartridge. The drive member is configured to engage the switch to create a detectable resistance at the axial position.

In embodiments, the stapler cartridge of the kit is a first staple cartridge, and the kit further includes a second stapler cartridge. The second stapler cartridge includes a second switch positioned at a second axial position different than the axial position of the switch on the first staple cartridge. The drive member is configured to engage the switch to create a detectable resistance at the second axial position. A reload detection mechanism may detect whether a stapler cartridge is mounted to the surgical instrument; whether the mounted stapler cartridge is unfired (or fresh) or has already been fired; and/or the type of the mounted stapler cartridge mounted to the end effector to ensure that the mounted stapler cartridge has a suitable staple length for the tissue to be stapled, based on the detectable resistance provided for at the different axial positions of the switch.

In another aspect, the present disclosure relates to a surgical stapling instrument comprising an end effector defining a longitudinal axis including a first jaw and a second jaw. The first jaw includes an anvil. The surgical stapling instrument further includes a drive member configured to translate distally and retract proximally through the end effector and an actuation mechanism configured to translate the drive member distally through the end effector and retract the drive member proximally through the end effector. The second jaw is configured to receive a stapler cartridge having an annular pin positioned within a channel formed in the stapler cartridge. The annular pin is movable from an unraised position to a raised position within the channel formed in the stapler cartridge.

In embodiments, the channel formed in the staple cartridge includes at least one interference structure formed therein. The interference structure is configured to retain the annular pin within the channel formed in the staple cartridge. In embodiments, the annular pin includes one or more undercuts formed thereon to engage with the interference structure to retain the annular pin within the channel formed in the staple cartridge.

In embodiments, the drive member engages the annular pin at an axial position. The annular pin is configured to provide for a detectable resistance upon engagement of the drive member at said axial position.

In embodiments, the surgical instrument is operatively coupled to a surgical system including a control unit, the control unit configured to process the detectable resistance to identify a type of reload present in the stapler cartridge.

In yet another aspect, the present disclosure relates to a surgical stapling instrument including a stapler cartridge having a switch. The surgical stapling instrument further includes an end effector defining a longitudinal axis including a first jaw and a second jaw. The first jaw includes an anvil and, the second jaw is configured to receive the stapler cartridge. The surgical stapling instrument further includes a drive member configured to translate distally through the end effector and an actuation mechanism configured to translate the drive member distally through the end effector. The surgical stapling instrument further includes a locking member movable from disabled position permitting distal translation of the drive member to at least an axial position where the drive member engages at least one of the staples, to a locking position inhibiting distal translation of the drive member to said axial position. The drive member is configured to contact the switch at an axial position of the drive member relative to the end effector. The switch is configured to provide a detectable resistance upon engagement of the drive member at said axial position.

In embodiments, the switch is movable from a first position wherein the switch maintains the locking member in the disabled position to a second position wherein the switch disengages from the locking member. In embodiments, the switch is positioned within a slot formed on a tail portion of the stapler cartridge.

In other embodiments, the drive member includes a knife, an inclined surface, and a chamfered surface. In embodiments, upon distal advancement of the drive member, the chamfered surface of the drive member engages a chamfered surface of the switch while the switch is in the first position.

In other embodiments, the switch comprises an annular pin positioned within a channel formed in the stapler cartridge. The annular pin is movable from an unraised position to a second raised position within the channel formed in the stapler cartridge. In embodiments, the channel formed in the staple cartridge includes at least one interference structure formed therein. The interference structure is configured to retain the annular pin within the channel formed in the staple cartridge. In embodiments, the annular pin includes one or more undercuts formed thereon to engage with the interference structure to retain the annular pin within the channel formed in the staple cartridge. In embodiments, engagement of the inclined distal portion of the drive member with the annular pin creates a detectable resistance.

In embodiments, the surgical instrument is operatively coupled to a surgical system including a control unit, the control unit configured to process the detectable resistance to identify the reload present in the stapler cartridge.

In yet another aspect, the present disclosure relates to a surgical stapling instrument including an end effector defining a longitudinal axis including a first jaw and a second jaw. The first jaw includes an anvil and the second jaw is configured to receive a stapler cartridge. The stapler cartridge includes a first and a second switch. The surgical stapling instrument further includes a drive member configured to translate distally through the end effector, and an actuation mechanism configured to translate the drive member distally through the end effector. The surgical stapling instrument further includes a locking member movable from disabled position permitting distal translation of the drive member to at least an axial position wherein the drive member engages at least one of the staples, to a locking position inhibiting distal translation of the drive member to said axial position. The drive member is configured to contact the first switch at an axial position of the drive member relative to the end effector. The first switch is configured to provide a detectable resistance upon engagement of the drive member at said axial position.

In embodiments, the first switch is an annular pin positioned within a channel formed in the stapler cartridge. The annular pin is movable from an unraised position to a second raised position within the channel formed in the stapler cartridge. The second switch is movable from a first position wherein the switch maintains the locking member in the disabled position to a second position wherein the switch disengages from the locking member.

BRIEF DESCRIPTION OF THE DRAWINGS

The above and other aspects, features, and advantages of the present surgical instruments having a locking mechanism will become more apparent in light of the following detailed description when taken in conjunction with the accompanying drawings in which:

FIG. 5 depicts a top view of a lockout assembly in accordance with the embodiment of FIG. 4 in the unlocked position;

FIG. 6 depicts a top view of a lockout assembly in accordance with the embodiment of FIG. 4 in the locked position;

FIG. 7 is a partial perspective view of an end effector in accordance with the embodiment of FIG. 4 including a lockout assembly in accordance with the embodiment of FIG. 5 showing a wedge of the drive member contacting a switch;

FIG. 12 is a top view of an end effector in accordance with the embodiment of FIG. 4 showing a drive member translated distally, a switch in the second position, and a locking member that is enabled;

FIG. 22 is a is a partial perspective side view of an illustrative end effector of a surgical instrument having an annular pin and a drive member positioned proximally of the annular pin;

FIG. 23 is a is a partial perspective side view of an illustrative end effector of a surgical instrument having an annular pin in an unraised position and a drive member engaging the annular pin upon being driven distally;

DETAILED DESCRIPTION

Particular embodiments of the present surgical instruments are described hereinbelow with reference to the accompanying drawings; however, it is to be understood that the disclosed embodiments are merely exemplary of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in any unnecessary detail.

While the following disclosure is presented with respect to a linear surgical stapler where staples are sequentially fired, it should be understood that features of the presently described surgical instruments may be readily adapted for use in any type of surgical clamping, cutting, or sealing instruments. The surgical clamping and cutting instrument may be a minimally invasive (e.g., laparoscopic) instrument or an instrument used for open surgery.

Additionally, the features of the presently described surgical stapling instruments may be readily adapted for use in surgical instruments that are activated using any technique within the purview of those skilled in the art, such as, for example, manually activated surgical instruments, powered surgical instruments (e.g., electro-mechanically powered instruments), robotic surgical instruments, and the like.

Figure 1:
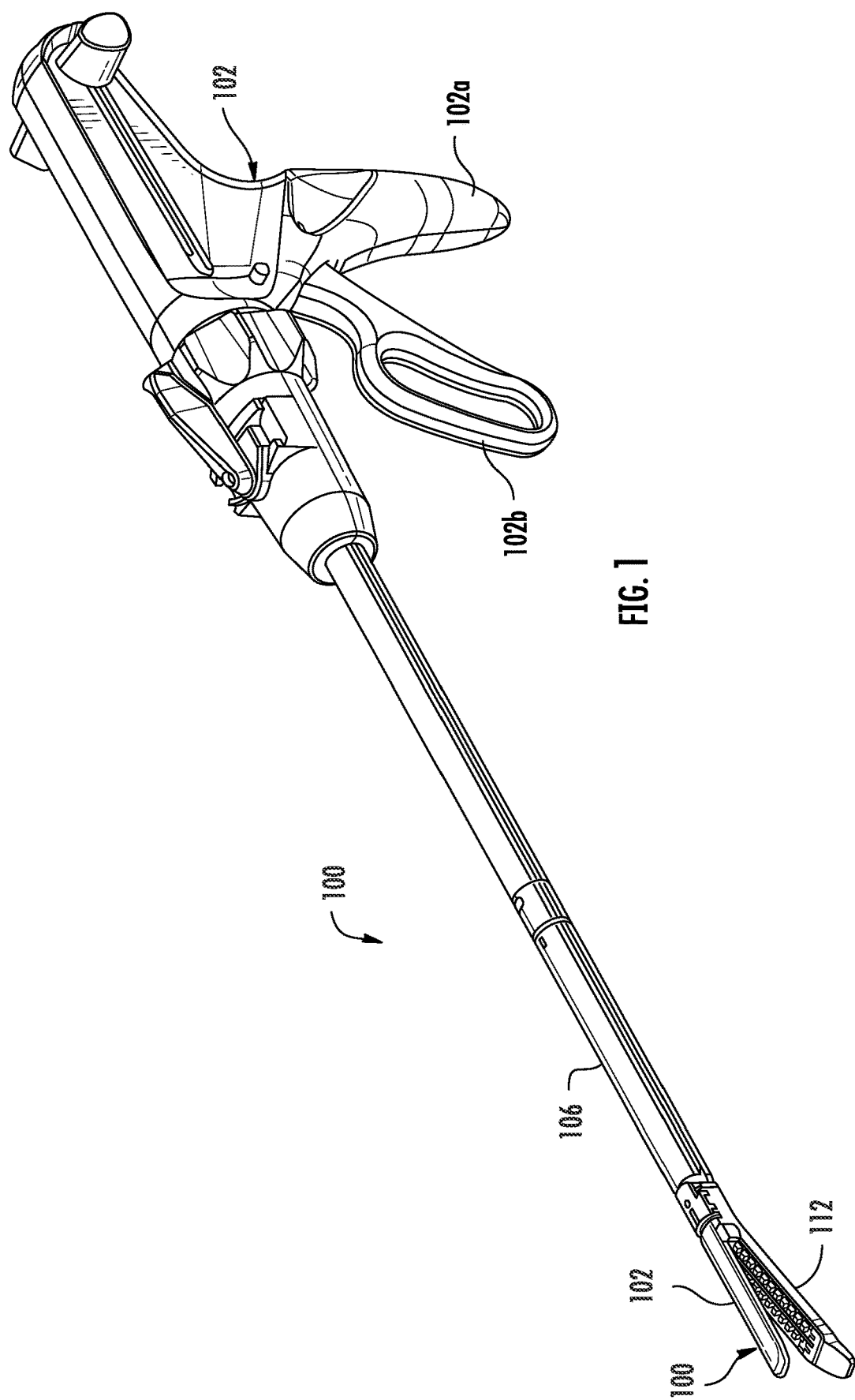
FIG. 1 is a perspective view of an illustrative surgical instrument having an end effector mounted to an elongated shaft, and an actuation mechanism.

FIG. 1 is a perspective view of an illustrative surgical instrument 100 in accordance with embodiments of the present disclosure having a handle assembly 102, and an end effector 110 mounted on an elongated shaft 106. End effector 110 includes a stationary jaw 111 and a moveable jaw 112. Handle assembly 102 includes a stationary handle 102a and a moveable handle 102b which serves as an actuator for surgical instrument 100.

In certain embodiments, handle assembly 102 may include input couplers (not shown) instead of, or in addition to, the stationary and movable handles. The input couplers provide a mechanical coupling between the drive tendons or cables of the instrument and motorized axes of the mechanical interface of a drive system. The input couplers may interface with, and be driven by, corresponding output couplers (not shown) of a telesurgical surgery system, such as the system disclosed in U.S. Pub. No. 2014/0183244A1, the entire disclosure of which is incorporated by reference herein. The input couplers are drivingly coupled with one or more input members (not shown) that are disposed within the instrument shaft 106. The input members are drivingly coupled with the end effector 110. Suitable input couplers can be adapted to mate with various types of motor packs (not shown), such as the stapler-specific motor packs disclosed in U.S. Pat. No. 8,912,746, or the universal motor packs disclosed in U.S. Pat. No. 8,529,582, the disclosures of both of which are incorporated by reference herein in their entirety. Further details of known input couplers and surgical systems are described, for example, in U.S. Pat. Nos. 8,597,280, 7,048,745, and U.S. Pat. No. 10,016,244. Each of these patents is hereby incorporated by reference in its entirety.

Actuation mechanisms of surgical instrument 100 may employ drive cables that are used in conjunction with a system of motors and pulleys. Powered surgical systems, including robotic surgical systems that utilize drive cables connected to a system of motors and pulleys for various functions including opening and closing of jaws, as well as for movement and actuation of end effectors are well known. Further details of known drive cable surgical systems are described, for example, in U.S. Pat. Nos. 7,666,191 and 9,050,119 both of which are hereby incorporated by reference in their entireties. While described herein with respect to an instrument configured for use with a robotic surgical system, it should be understood that the wrist assemblies described herein may be incorporated into manually actuated instruments, electro-mechanical powered instruments, or instruments actuated in any other way.

Figure 2:
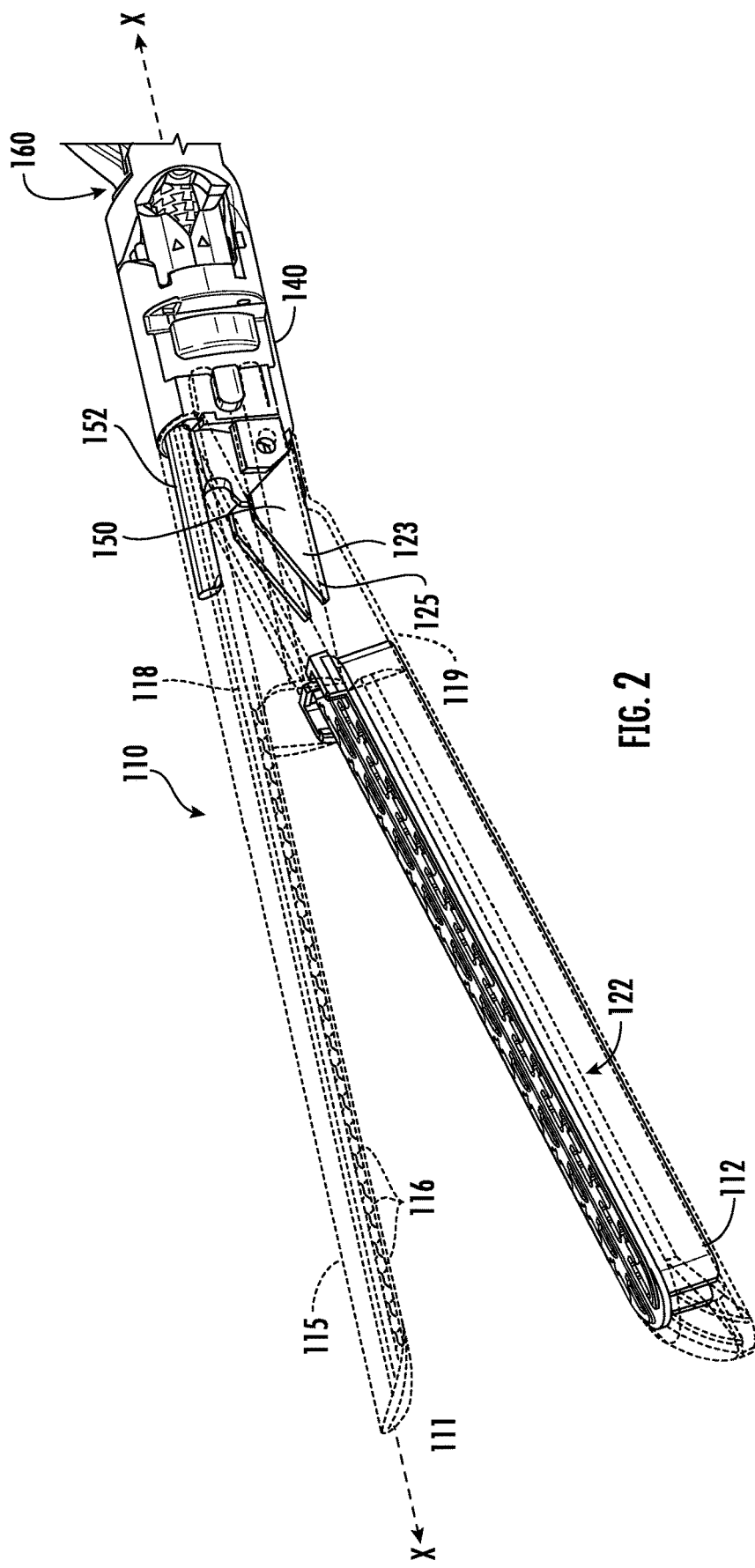
FIG. 2 is a perspective view of the distal end portion of an illustrative surgical instrument in accordance with the present disclosure with the jaws in the open position.

FIG. 2 shows the distal end portion of surgical instrument 100, including an end effector 110 defining a longitudinal axis X-X and having a first jaw 111, a second jaw 112, a clevis 140 for mounting jaws 111, 112 to the instrument, and an articulation mechanism, such as a wrist assembly 160. In certain embodiments, second jaw 112 is a movable jaw configured to move from an open position to a closed position relative to first jaw 111. In other embodiments, first jaw 111 is a movable jaw configured to move between open and closed positions relative to second jaw 112. In still other embodiments, both jaws 111, 112 are movable relative to each other. First jaw 111 includes an anvil 115 having staple-forming pockets 116. In the exemplary embodiment, first jaw 112 is a movable jaw 112 configured to move from an open position to a closed position relative to stationary jaw 111. In the open position, a fresh stapler cartridge 122 (sometimes referred to as a fresh or unfired reload) can be loaded into movable jaw 112 and tissue may be positioned between the jaws 111, 112. In the closed position, jaws 111, 112 cooperate to clamp tissue such that stapler cartridge 122 and the anvil 115 are in close cooperative alignment.

Figure 3:
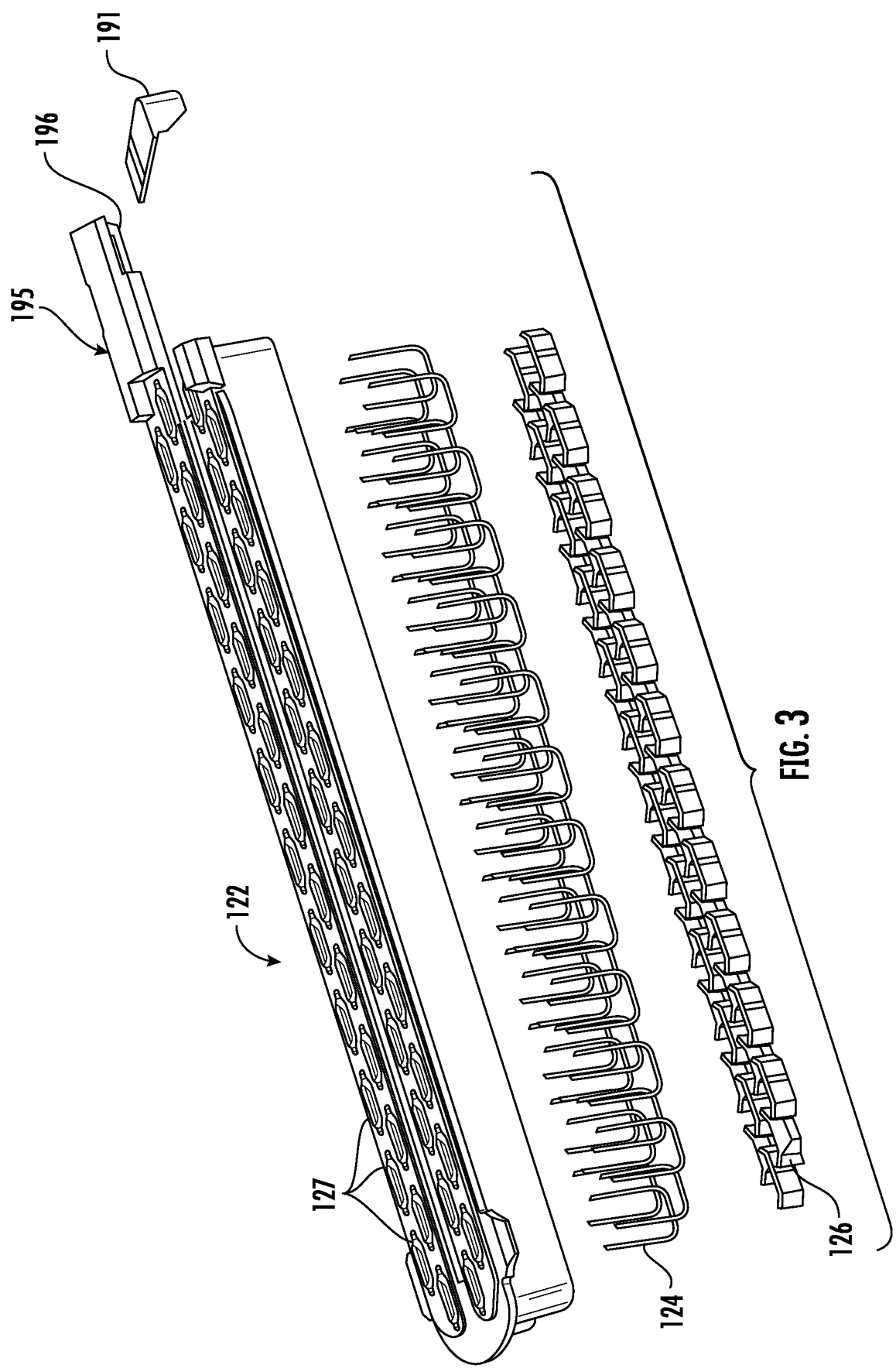
FIG. 3 is an exploded view of a cartridge configured for use with the surgical instrument of FIG. 1 including surgical fasteners, staple drivers, and a switch.
Figure 8:
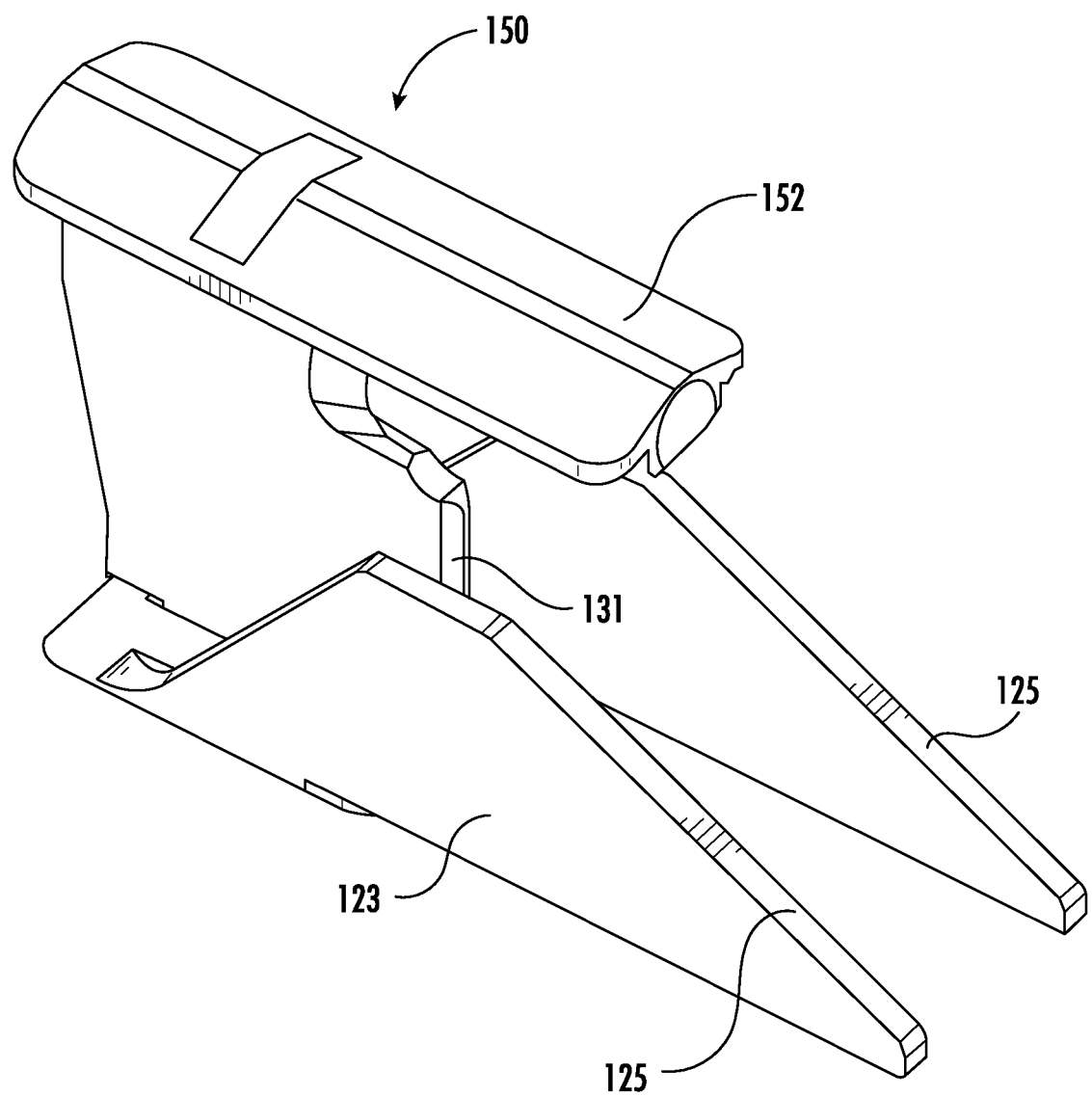
FIG. 8 depicts a perspective view of an illustrative drive member in accordance with the embodiment of FIG. 4.

As shown in FIG. 3, stapler cartridge 122 may include a plurality of staples 124 supported on corresponding staple drivers 126 provided within respective staple retention openings 127 formed in stapler cartridge 122. As shown in FIG. 8, end effector 110 may also include a drive member 150 configured to translate distally and retract proximally through the end effector, the drive member may have a shuttle 123 integrally formed thereon including an inclined distal portion 125 that sequentially acts on staple drivers 126 upon distal movement of the drive member 150, camming staple drivers 126 upwardly, thereby moving staples 124 into deforming contact with anvil 115. In embodiments, shuttle 123 may be included within stapler cartridge 122 as a separate component. In embodiments, stapler cartridge 122 further includes one or more switches configured to engage a slot 196 formed on the proximal tail 195 of stapler cartridge 122. The functionality of switches 191 will be described in more detail below. As seen in FIG. 8, drive member 150 includes an upper shoe 152 that is substantially aligned with and translates through a channel in fixed jaw 111 (see FIG. 2), while lower shoe 154, also seen in FIG. 8, of drive member 150 translates through and underneath jaw 112. The details of the drive member and actuation will be described below.

Figure 4:
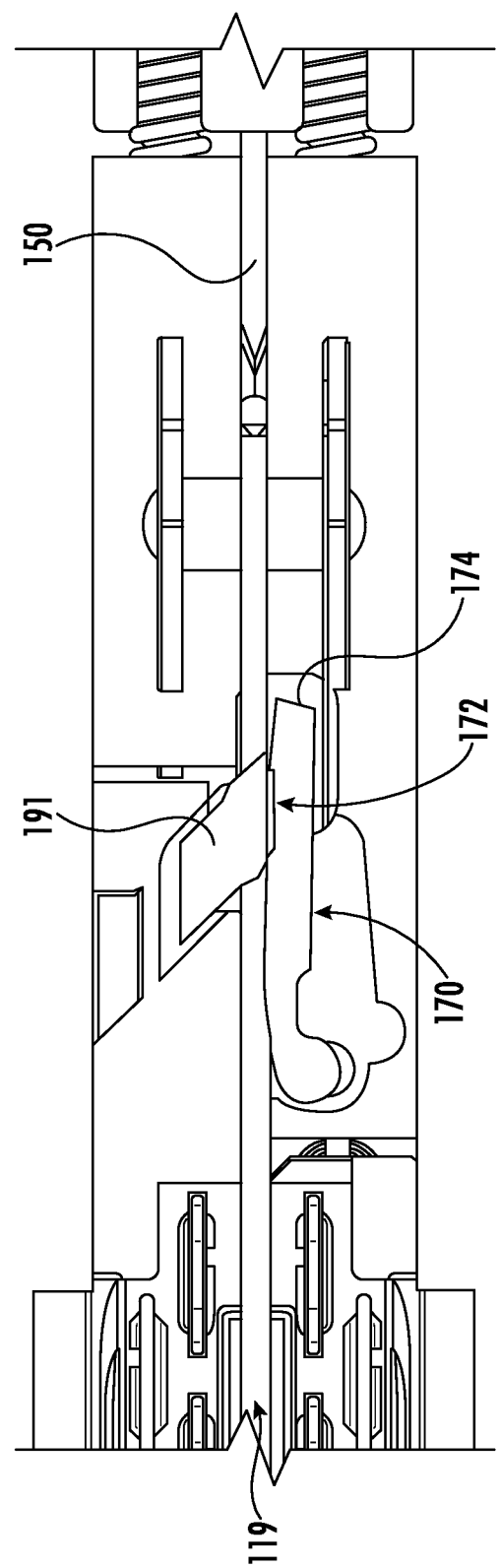
FIG. 4 depicts a partial top view of the end effector of a surgical stapling instrument including a lockout assembly in accordance with an embodiment of the present disclosure having an unfired reload installed.

FIG. 4 shows a portion of an illustrative surgical instrument with an unfired reload installed, including portions of stapler cartridge 122, a locking member 170, and switch 191.

When an unfired reload is installed, as shown in FIG. 4, switch 191 is in a first home (or default) position. In a fresh, unfired reload, switch 191 is in contact with switch engaging portion 172 of locking member 170, keeping engagement portion 174 out of channel 119. When locking member 170 is in this disabled position, distal translation of drive member 150 is permitted, as locking member 170 will not obstruct movement of drive member 150 because engagement portion 174 is held out of alignment with channel 119.

FIGS. 5 and 6 show a top view of a locking assembly including a locking member 170 in the unlocked or disabled position and the locked position, respectively with switch 191 not shown.

Locking member 170 pivots about a pivot point 179 that is laterally offset from channel 119. Locking member 170 is configured to move in a direction substantially perpendicular to the longitudinal axis of the end effector. Spring 178 biases engagement portion 174 of locking member 170 into channel 119 to lock the instrument. In the unlocked position of FIG. 5, switch 191 (see FIG. 4) engages switch engaging portion 172 of locking member 170, overcoming the bias of spring 178 and holding engagement portion 174 out of channel 119, permitting distal movement of drive member 150. When switch 191 is no longer in contact with switch engaging portion 172 of locking member 170, spring 178 forces engagement portion 174 of locking member into channel 119 as seen in FIG. 6, where engagement portion 174 obstructs distal movement of drive member 150.

Figure 9:
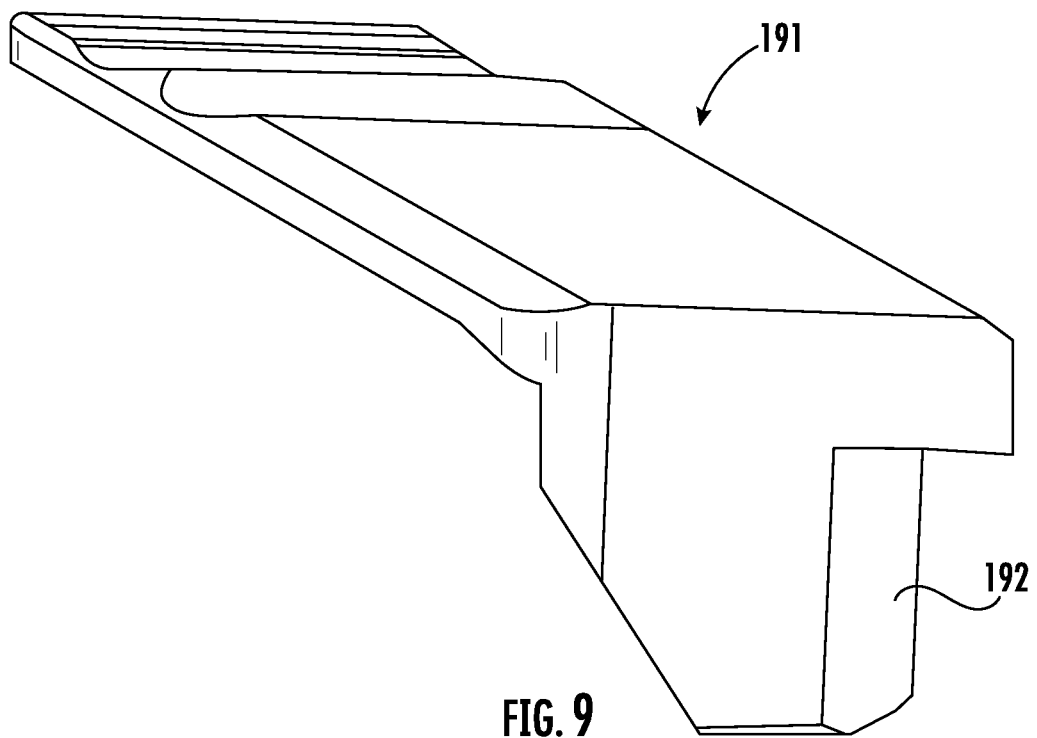
FIG. 9 depicts a perspective view of an illustrative switch in accordance with the lockout assembly of FIG. 4.

FIG. 7 shows a view of an end effector in accordance with the embodiment of FIG. 4 including a lockout assembly in accordance with the embodiment of FIG. 5. In FIG. 7, a fresh reload has been installed, and switch 191 is in the initial position. Locking member 170 is held by switch 191 out of channel 119 so that, upon actuation, drive member 150 may be advanced distally along channel 119. As shown in FIG. 7, upon distal translation of drive member 150 during actuation of the instrument, a chamfered surface 131 formed on drive member 150 (as seen in FIG. 8) engages a chamfered surface 192 formed on switch 191 (as seen in FIG. 9). Switch 191 is then driven through a switch channel 129 in a direction substantially perpendicular to the longitudinal axis of end effector 110.

Figure 11:
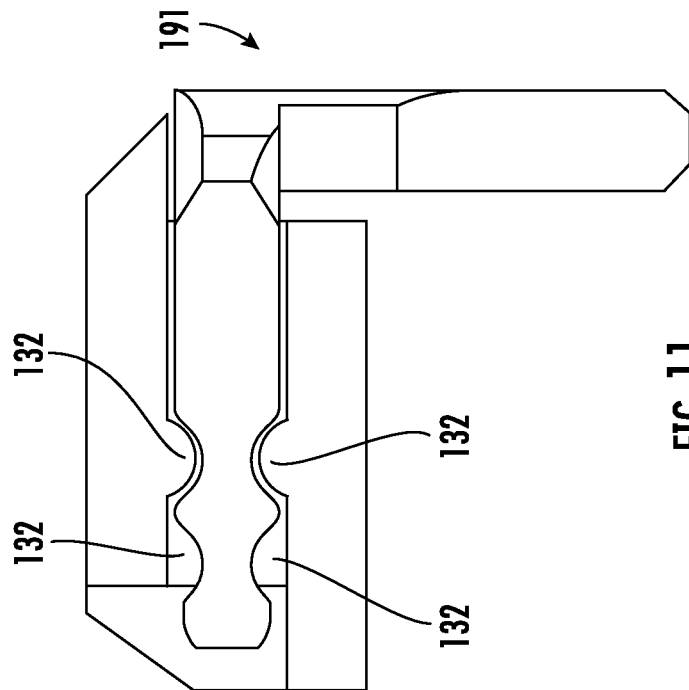
FIG. 11 depicts a partial perspective view of an illustrative switch in accordance with the embodiment of FIG. 4 in the second position after engagement with a drive member.
Figure 10:
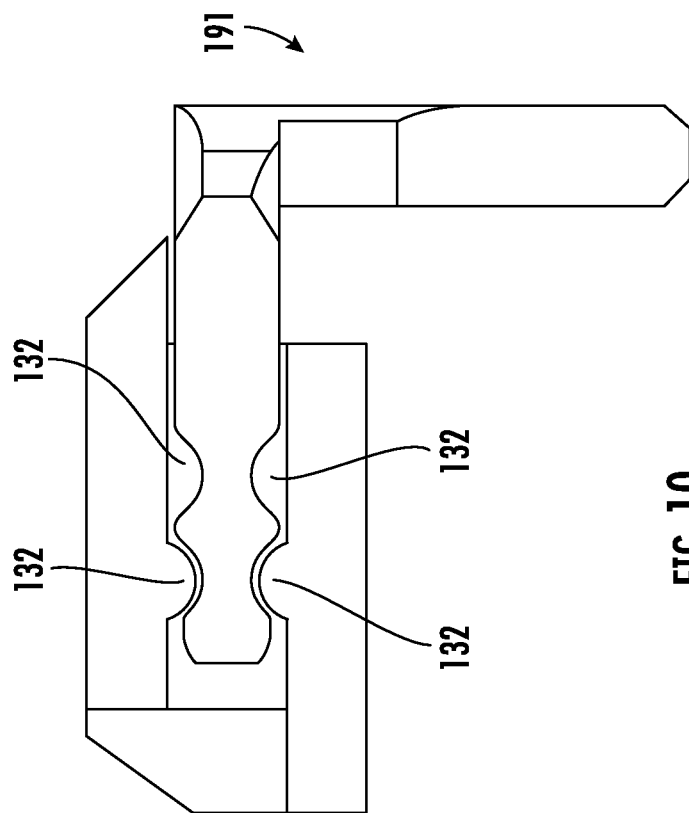
FIG. 10 depicts a partial perspective view of an illustrative switch in accordance with the embodiment of FIG. 4 in the initial position after a fresh stapler cartridge has been installed.

In FIG. 10, switch 191 is shown in the initial position within switch channel 129 (see FIG. 7). Switch channel 129 includes a series of detents 132 configured to provide mechanical resistance that must be overcome by drive member 150 in order to slide switch 191 from the initial position toward the second position, shown in FIG. 11. This ensures that the lockout will not unintentionally activate as may happen if switch 191 freely slides in channel 129 (e.g., in the absence of detents 132). In embodiments, switch 191 may secured by friction fit within switch channel 129. As best seen in previously described FIG. 7, while drive member 150 translates distally along the longitudinal axis defined by end effector 110, switch 191 moves laterally through channel 129 in a direction perpendicular to the axis. This allows switch 191 to be retained the within end effector 110 on a side that is opposite locking member 170, such that switch 191 and locking member 170 do not have to compete for space within end effector 110, allowing for maintenance of reduced instrument size.

Figure 13:
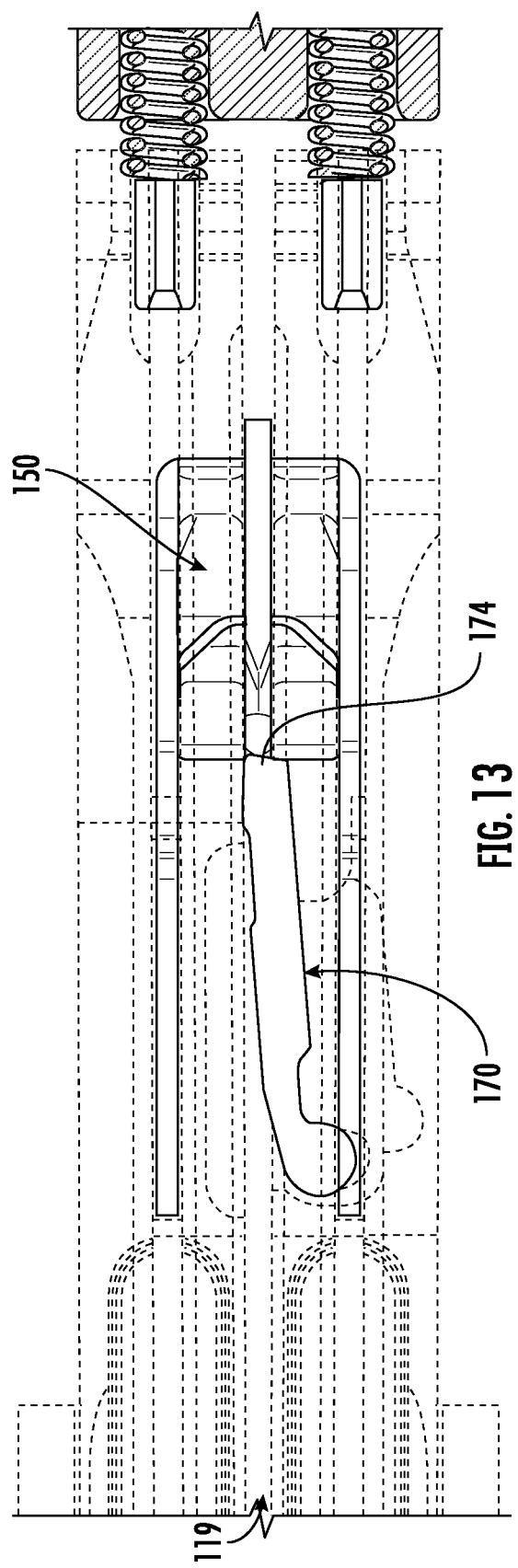
FIG. 13 is a top view of an end effector in accordance with the embodiment of FIG. 4 showing a drive member that has been fully retracted after firing, and a locking member that is enabled.
Figure 14:
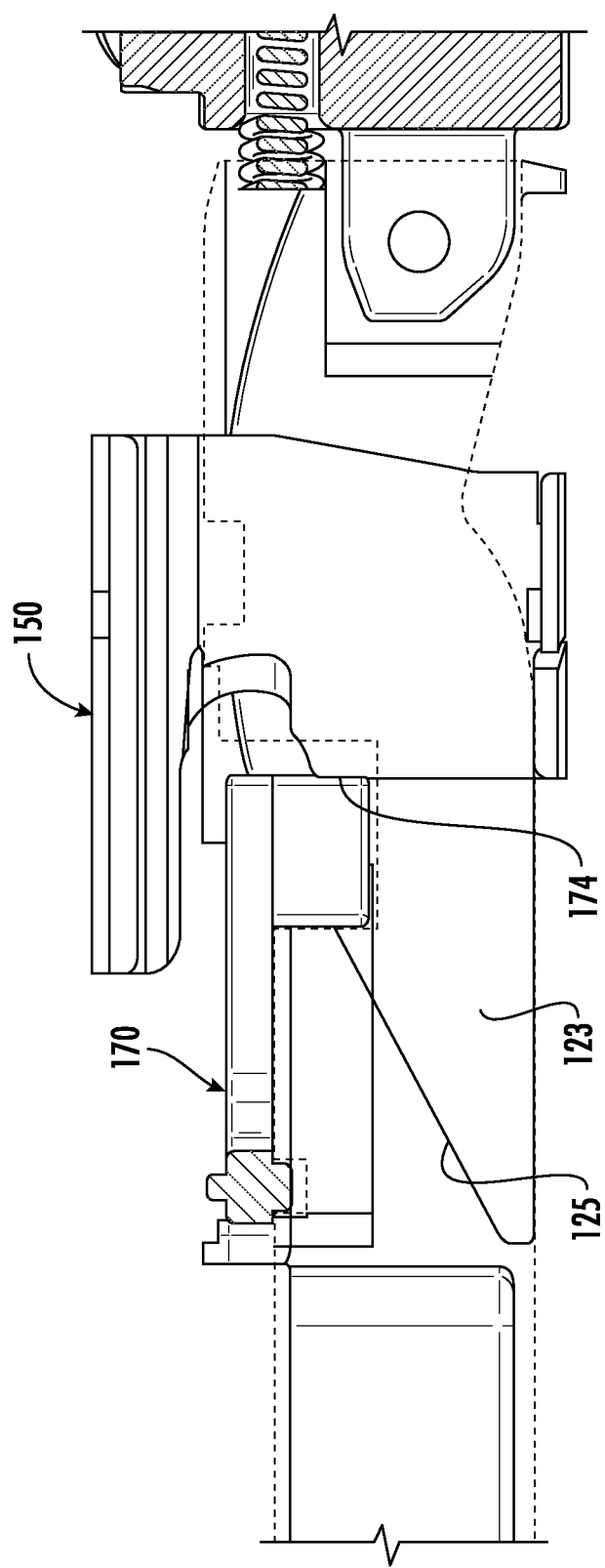
FIG. 14 is a partial perspective side view of an end effector in accordance with the embodiment of FIG. 4 showing a drive member that has been fully retracted after firing, and a locking member that is enabled.

In FIG. 12 drive member 150 has translated distally, forcing switch 191 to the second position thereby enabling locking member 170 as spring 178 biases engagement portion 174 of locking member 170 into channel 119. Drive member 150 may continue to travel distally to drive staples into tissue and cut the stapled tissue. Upon retraction, drive member 150 engages a series of proximal ramped surfaces 176 on locking member 170, allowing drive member 150 to return to a position proximal of locking member 170. However, once drive member 150 is positioned proximally of locking member 170, if another attempt is made to actuate the instrument, drive member 150 will be obstructed by engagement portion 174 of locking member 150, preventing actuation of an unloaded instrument, as best seen in FIGS. 13 and 14.

Figure 15:
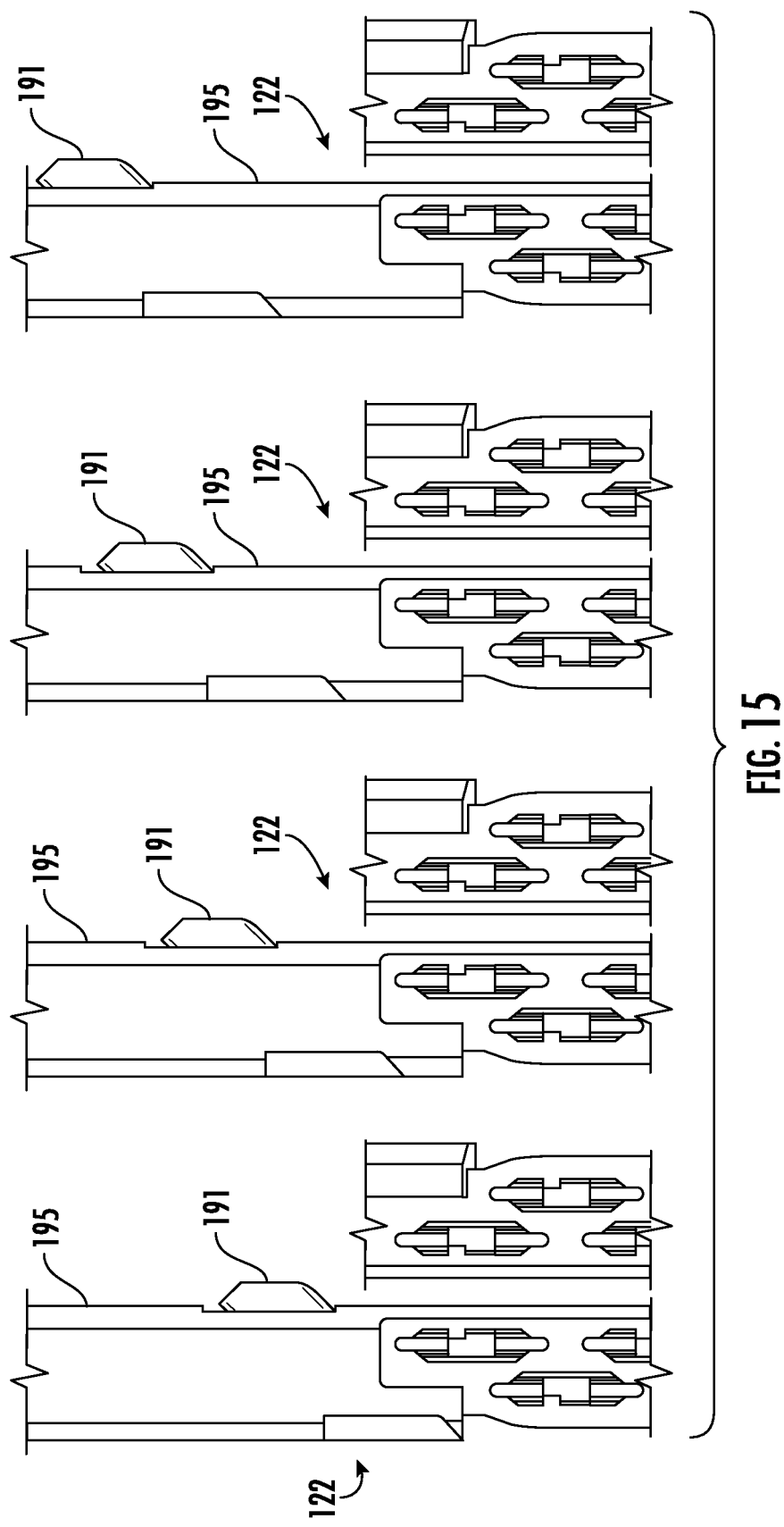
FIG. 15 is a partial top view of the proximal ends of a series of illustrative stapler cartridges having a switch in the initial position at various axial positions on the respective tail of each stapler cartridge.

FIG. 15 shows a series of illustrative cartridges having a switch 191 in the initial position at various axial positions on the respective tail 195 of each stapler cartridge 122. In embodiments, the axial position of switch 191 may function as a mechanism by which a robotic surgical system may identify the type of stapler cartridge installed. As drive member 150 translates through the end effector, it will encounter the switch at a distinct axial position for a given type of stapler cartridge. When the drive member encounters the switch, the drive member will encounter a detectable amount of resistance. In embodiments, a robotic surgical system may be configured to detect the position along a firing stroke at which the chamfered surface 131 formed on drive member 150 engages switch 191 via detection of a torque spike, allowing the system to determine the type of stapler cartridge installed. This will allow a control unit, operatively coupled with the actuation mechanism, to determine the correct amount of forces to apply to the drive member depending upon the features of the detected type of stapler cartridge, including but not limited to, the number of staples contained therein, the size of the staples contained therein, and the geometry of the staples contained therein. An exemplary surgical stapler including a surgical system including a control unit operatively coupled to the actuation mechanism is described for example in International Application No. PCT/US2017050747, the disclosure of which is hereby incorporated by reference in its entirety.

Figure 16:
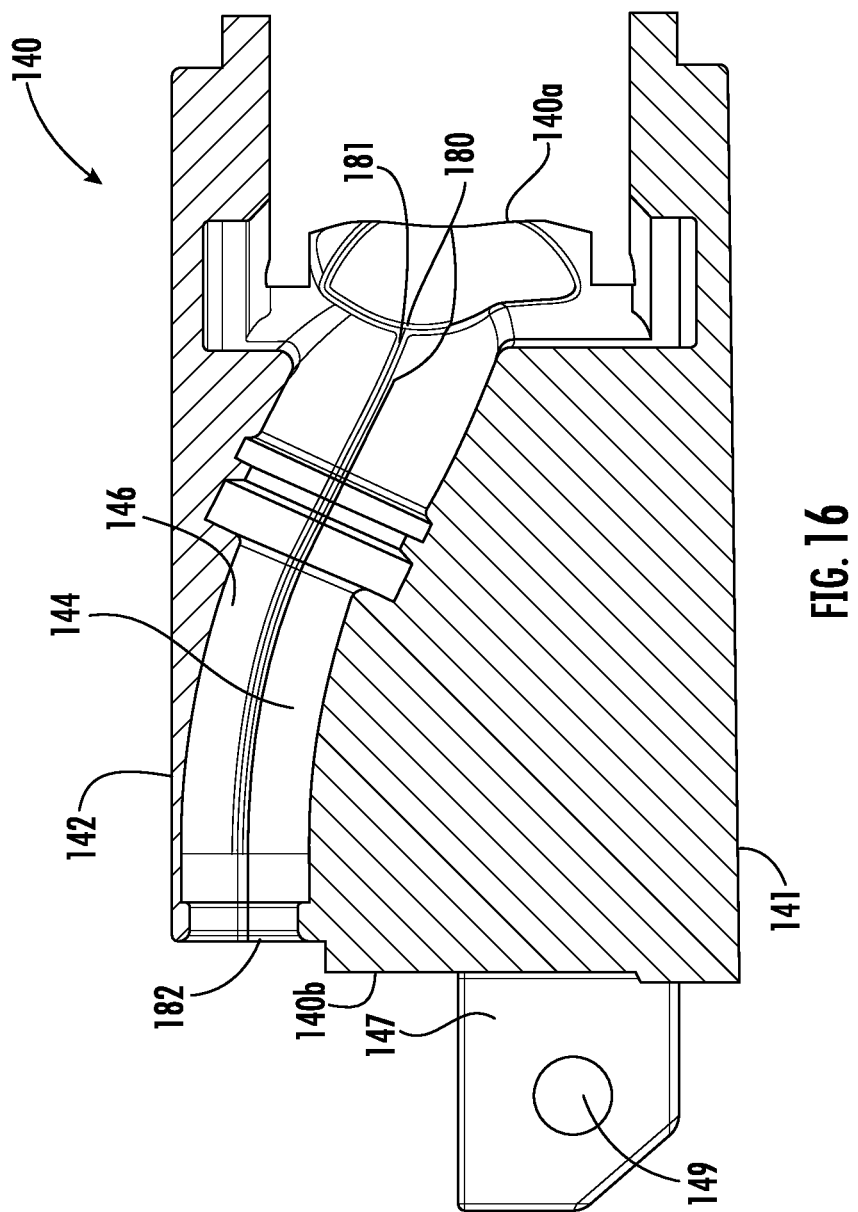
FIG. 16 is a cross-sectional side of a two-part clevis of the surgical instrument of FIG. 1.

Jaws 111, 112 are attached to surgical instrument 100 via clevis 140. See, FIG. 16. Clevis 140 includes a proximal surface 140a and a distal surface 140b. Clevis 140 further includes upper clevis portion 142 and lower clevis portion 141 that cooperate when assembled to form protrusion 145 (see FIG. 20A) configured to engage tabs 113 (seen in in FIG. 20A of jaw 111 to securely mount jaw 111 in a fixed position on instrument 100. As seen in FIG. 16, Lower clevis portion 141 includes a pair of distally extending arms 147 for supporting movable jaw 112. Arms 147 include opening 149 for receiving a pivot pin 130 defining a pivot axis around which jaw 112 pivots as described in more detail below. Lower clevis portion 141 also includes ramped groove 144 configured to guide a portion of an actuation coil 120 (see FIG. 19A) emerging from wrist 160 (see FIG. 17). Upper clevis portion 142 includes a complementary shaped ramped groove 146 that cooperates with ramped groove 144 of lower clevis portion 141 to form an enclosed channel 180 that guides coil 120 as it jogs upwards from wrist 160 towards distal surface 157 of upper shoe 152 of drive member 150. In embodiments, channel 180 may include a first end 181 at a central portion of proximal surface 140a and a second end 182 at a peripheral portion of distal surface 140b. In embodiments, enclosed channel 180 may be substantially "S" shaped. Although shown as a two-part clevis, it should be understood that the clevis may be a unitary structure formed, for example, by molding, machining, 3-D printing, or the like.

Figure 17:
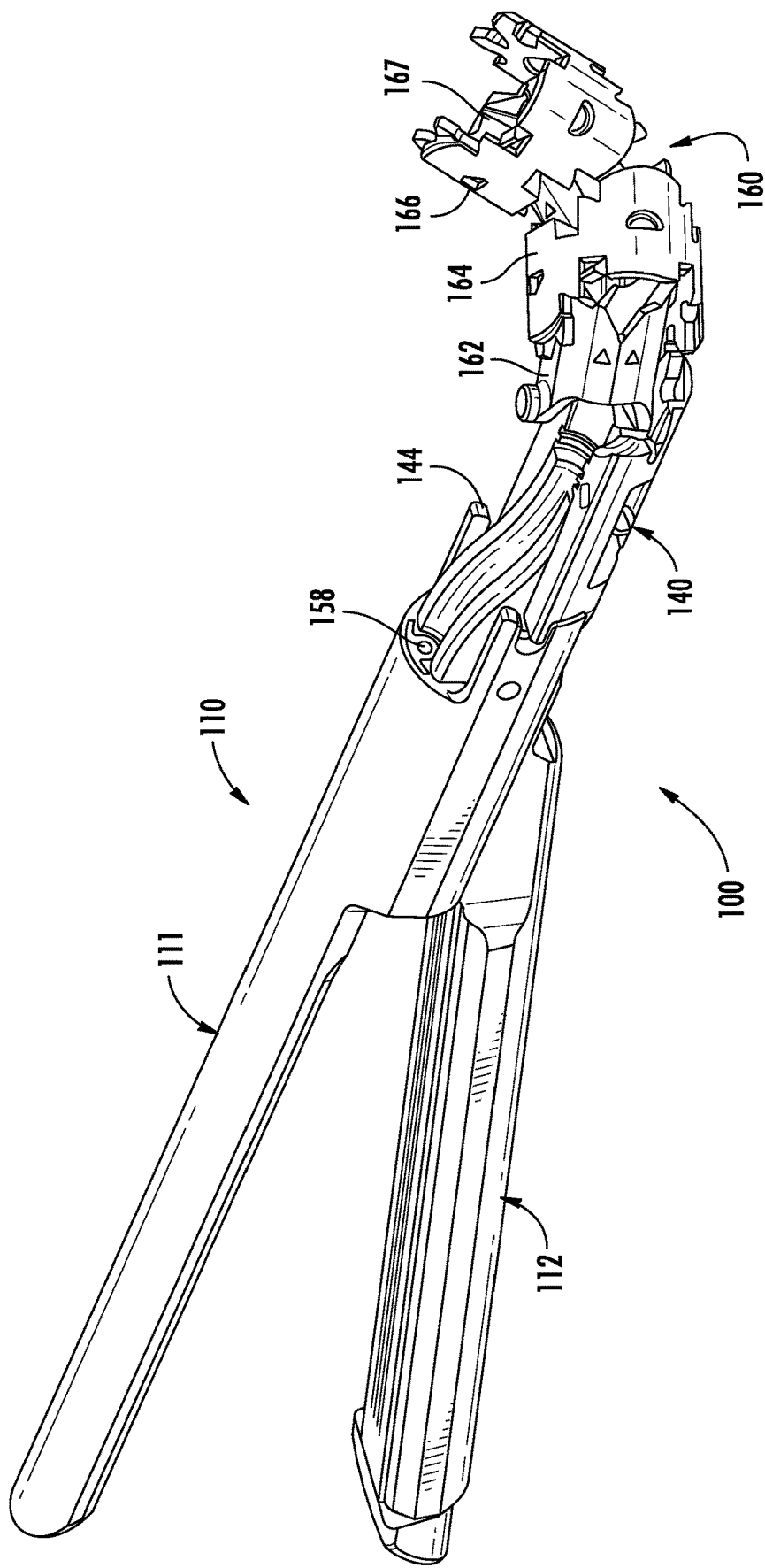
FIG. 17 is a perspective view of the end portion of an illustrative surgical instrument with parts removed.

End effector 110 may be articulated in multiple directions by an articulation mechanism. In embodiments, the articulation mechanism may be a wrist 160 as shown, although other articulation mechanisms are contemplated. As seen in FIG. 17, wrist 160 includes a plurality of articulation joints 162, 164, 166, etc. that define a bore 167 through which an actuation mechanism (in embodiments, coil 120 and drive cable 171, see FIG. 19A) may pass. Upon exiting articulation wrist 160, coil 120 enters and passes through channel 180 of clevis 140 (see FIG. 18), ultimately engaging proximal surface 153 of upper shoe 152 of drive member 150. Other articulation mechanisms within the purview of those skilled in the art may substitute for wrist 160. One suitable articulation mechanism is described for example in U.S. Publication No. 2015/0250530, the disclosure of which is hereby incorporated by reference in its entirety.

Upon actuation of the surgical instrument, drive member 150 is advanced distally through end effector 110 to move jaws 111, 112 from the open position to the closed position, after which shuttle 123 and knife 128 are advanced distally through cartridge 122 to staple and cut tissue grasped between jaws 111, 112. Drive member 150 may be any structure capable of pushing at least one of a shuttle or a knife of a surgical stapling instrument with the necessary force to effectively sever or staple human tissue. Drive member 150 may be an I-beam, an E-beam, or any other type of drive member capable of performing similar functions. Drive member 150 is movably supported on the surgical stapling instrument 100 such that it may pass distally through cartridge 122 and upper fixed jaw 111 and lower jaw 112 when the surgical stapling instrument is fired (e.g., actuated).

Figure 18:
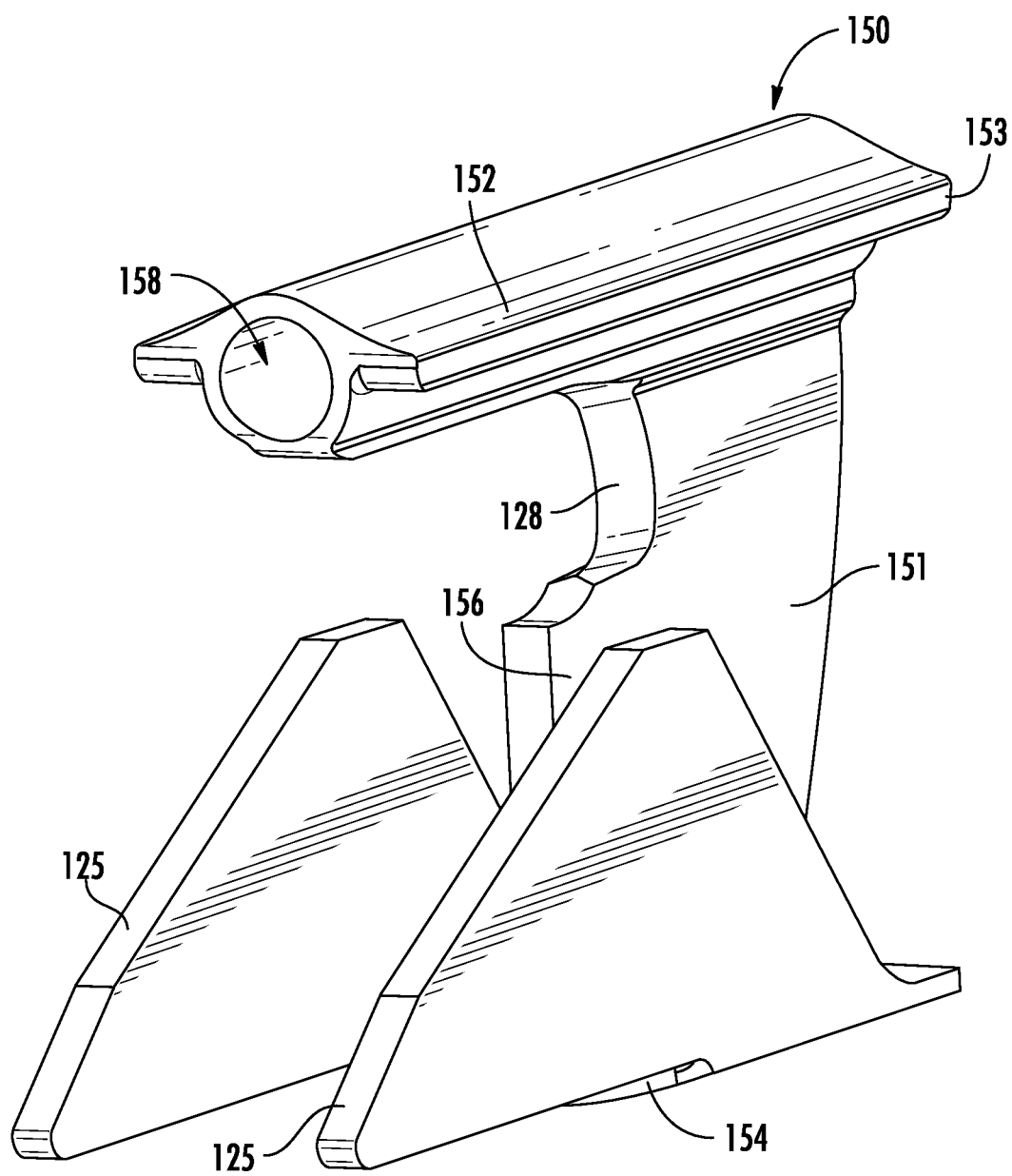
FIG. 18 is a perspective view of a drive member in accordance with the illustrative surgical instrument of FIG. 1.

As seen in FIG. 18, drive member 150 may include a body 151, upper shoe 152, lower shoe 154, and central portion 156. Upper shoe 152 of drive member 150 is substantially aligned with and translates through a channel 118 in fixed jaw 111, while lower shoe 154 of drive member 150 is substantially aligned with and translates through a channel 119 and below jaw 112. Bore 158 is formed through upper shoe 152 to receive drive cable 171 as will be described in more detail below. Proximal surface 153 of upper shoe 152 is configured to be engaged by a coil 120 of actuation assembly 190 such that coil 120 may apply force to upper shoe 152 to advance drive member 150 distally, i.e., in the direction of arrow "A" in FIG. 19B. A knife 128 may be formed on drive member 150 along the distal edge between upper shoe 152 and central portion 156. In embodiments, inclined distal portions 125 may be formed on either side of drive member 150.

Actuation assembly 190 includes a drive cable 171, a coil 120, a sheath 121 surrounding coil 120, and a drive rod 175. Drive cable 171 includes an enlarged distal end 173.

Figure 19A:
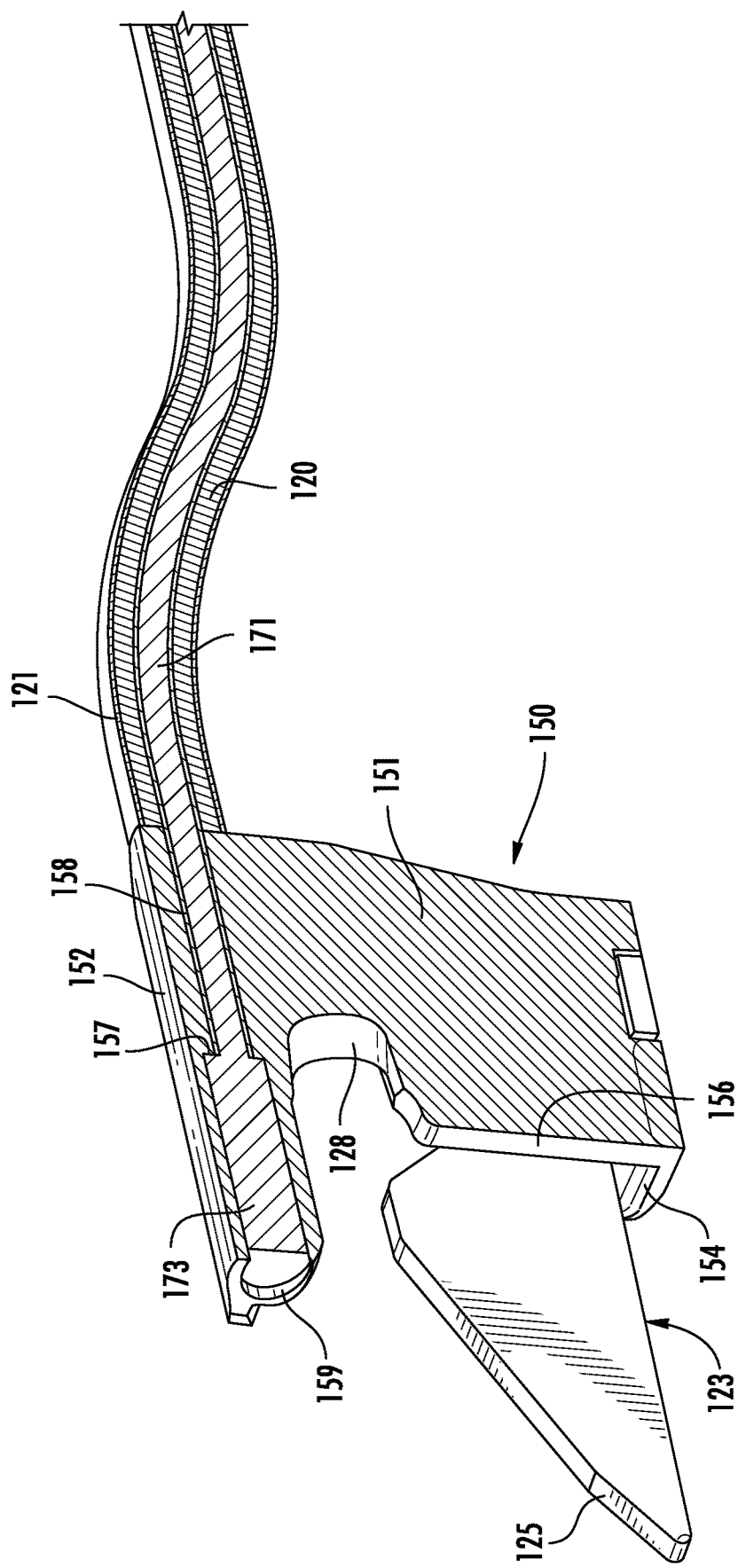
FIG. 19A is a cross-sectional perspective view of the actuation mechanism for a drive member in accordance with the surgical instrument of FIG. 1.
Figure 19B:
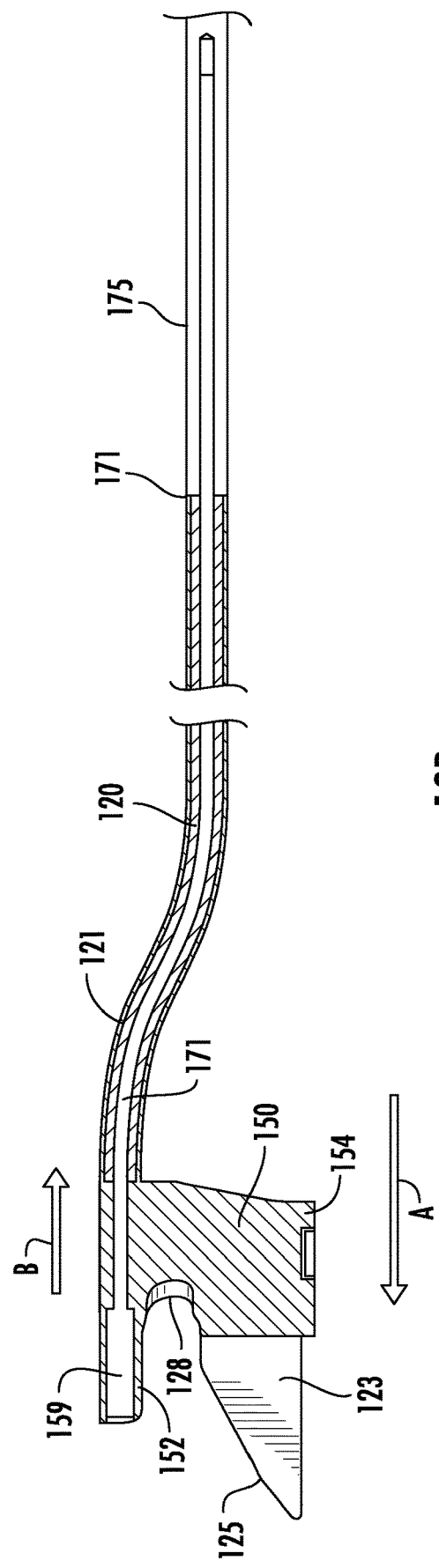
FIG. 19B is a cross-sectional side view of the actuation mechanism for a drive member in accordance with the surgical instrument of FIG. 1.

As seen in FIGS. 19A and 19B, upper shoe 152 of drive member 150 includes a bore 158 into which drive cable 171 is routed. When assembling illustrative surgical instrument 100, coil 120 and a protective sheath 121 are slipped over the free end of drive cable 171. The free end of drive cable 171 is attached to a drive rod 175 securing coil 120 and the protective sheath 121 between drive member 150 and drive rod 175 as seen in FIG. 19B. Sheath 121 may function to promote stability, smooth movement, and prevent buckling upon actuation of surgical instrument 100. Sheath 121 may be made from polyimide, or any other suitable material having the requisite strength requirements such as various reinforced plastics, a nickel titanium alloy such as NITINOL™, poly para-phenyleneterphtalamide materials such as KEVLAR™ commercially available from DuPont. Other suitable materials may be envisioned by those of skill in the art. Enlarged distal end 173 of drive cable 171 resides within an enlarged distal portion 159 of bore 158 in upper shoe 152 of body 150, such that the proximal face 157 of enlarged distal end 173 may apply a retraction force on upper shoe 152 when the drive cable 171 is pulled proximally, i.e., in the direction of arrow "B" in FIG. 19B. Drive rod 175 is operationally connected to an actuator (e.g., movable handle 102b), which allows distal translation and proximal retraction of actuation assembly 190. Those skilled in the art will recognize that in a manually actuated instrument, the actuator may be a movable handle, such as moveable handle 102b shown in FIG. 1; in a powered instrument the actuator may be a button (not shown) that causes a motor to act on the drive rod; and in a robotic system, the actuator may be a control device such as the control devices described below in connection with FIG. 28. Any suitable backend actuation mechanism for driving the components of the surgical stapling instrument may be used. For additional details relating to exemplary actuation mechanisms using push/pull drive cables see, e.g., commonly owned International Application WO 2018/049217, the disclosure of which is hereby incorporated by reference in its entirety.

During actuation of illustrative surgical instrument 100, drive rod 175 applies force to coil 120, thereby causing coil 120 to apply force to upper shoe 152 of drive member 150, translating it distally (i.e., in the direction of arrow "A" in FIG. 19B) initially closing jaws 111,112 and then ejecting staples 124 from cartridge 122 to staple tissue. After stapling is complete, drive rod 175 applies a force in the proximal direction to effect retraction of drive member. During retraction, enlarged distal end 173 of drive cable 171 is obstructed by wall 157 of enlarged portion 159 of bore 158, causing drive cable 171 to apply force to upper shoe 152 of drive member 150, thereby translating drive member 150 in the proximal direction. In certain embodiments, the surgical instrument may be designed such that the drive member 150 is not retracted in the proximal direction after the staples have been fired. One of ordinary skill in the art will appreciate that drive member 150, drive cable 171, and drive rod 175 all move in unison and remain in the same relative position to each other.

In the preferred embodiment, drive cable 171 advances drive member 150 through fixed jaw 111 (instead of through the staple cartridge jaw as in conventional surgical stapling instruments). Eliminating the internal channel for the actuation mechanism from the staple cartridge provides more space in the cartridge for the staples and for the reinforcing wall discussed above. In alternative embodiments, coil 120 of actuation assembly 190 may be coupled with lower shoe 154 instead of upper shoe 152. In these embodiments, coil 120 applies force to lower shoe 153 to advance drive member 150 distally through a channel (not shown) in the lower jaw 112. In these embodiments, coil 120 will advance at least through a portion of lower jaw 112 and staple cartridge 122.

Figure 20A:
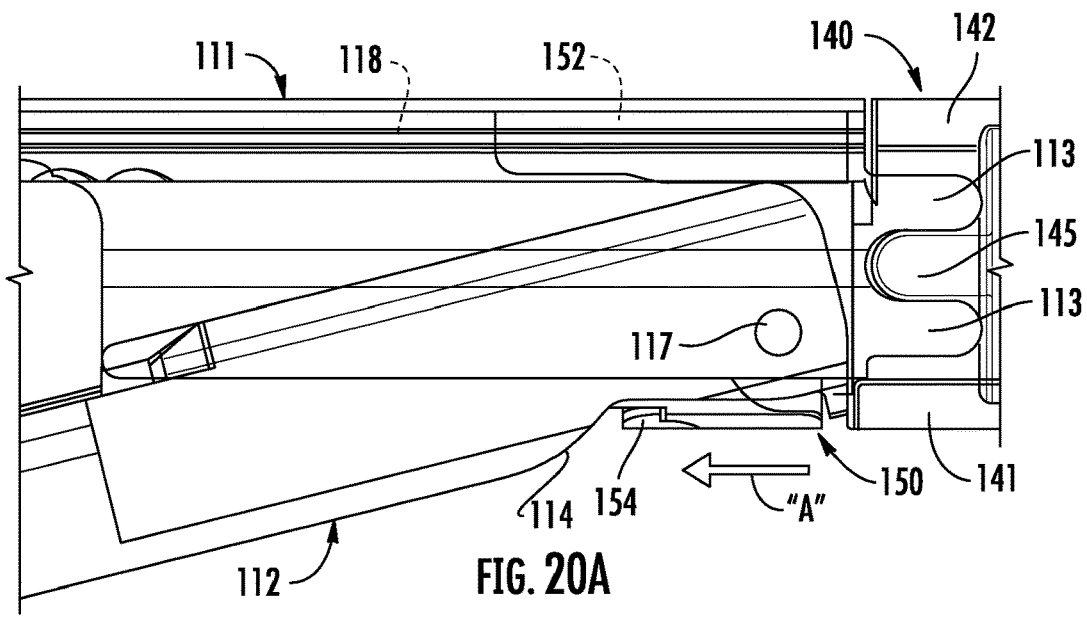
FIG. 20A shows a movable lower jaw of an illustrative surgical instrument in an open configuration.
Figure 20B:
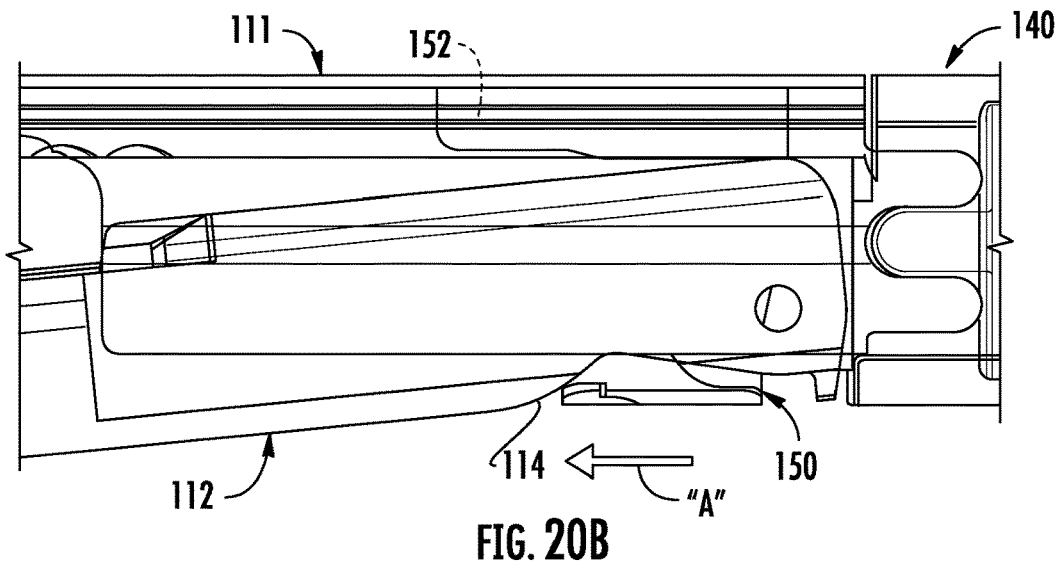
FIG. 20B shows a movable lower jaw of an illustrative surgical instrument pivoting towards a closed position.
Figure 20C:
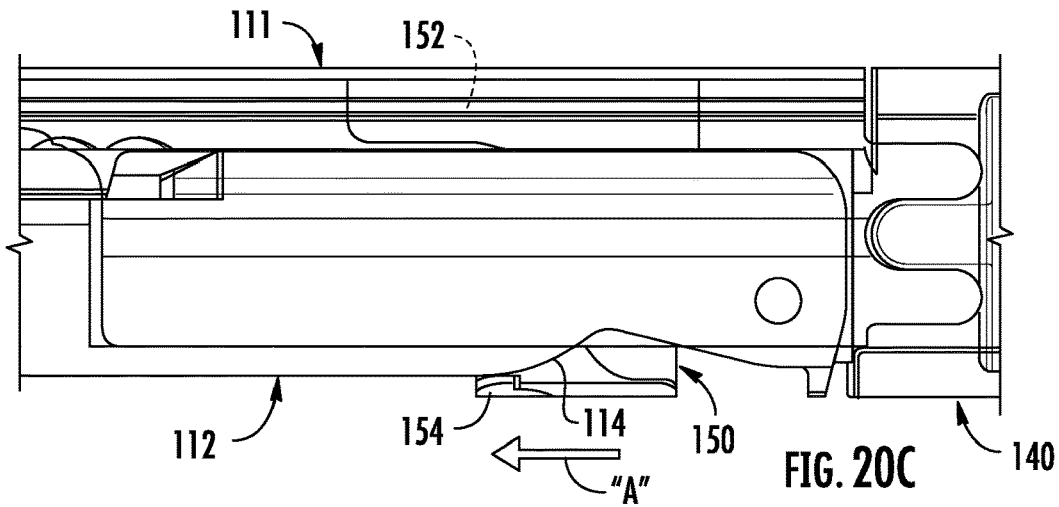
FIG. 20C shows a movable lower jaw of an illustrative surgical instrument in a closed position.

FIGS. 20A-C depict fixed jaw 111 and movable jaw 112 of illustrative surgical instrument 100 sequentially moving from an open configuration to a closed configuration. As shown in FIG. 20A, in the open configuration, drive member 150 is positioned proximally of cam surface 114 formed on movable jaw 112. As drive member 150 translates in the distal direction "A" movable jaw 112 will rotate towards the closed position around pivot 117.

In FIG. 20B, drive member 150 has come into contact with cam surface 114 of movable jaw 112. As lower portion 154 of drive member 150 rides underneath cam surface 114, drive member 150 pushes movable jaw 112, causing it to pivot towards the closed position.

FIG. 20C illustrates jaws 111, 112 in the closed position. Drive member 150 has translated distally past cam surface 114. In this position, tissue is clamped, and further advancement of the drive member will sever and staple tissue.

Figure 21:
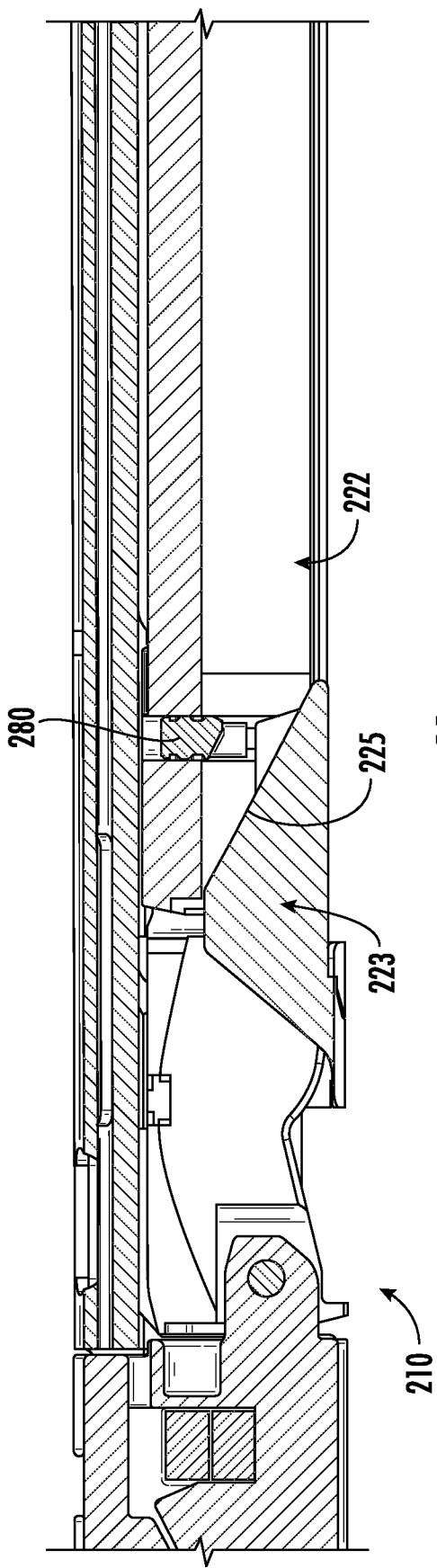
FIG. 21 is a partial perspective side view of an illustrative end effector of a surgical instrument having an annular pin.

FIG. 21 illustrates an alternative embodiment in which an illustrative end effector 210 has a stapler cartridge 222 installed therein. Stapler cartridge 222 includes an annular pin 280 configured to be engaged by an inclined distal portion 225 of an illustrative shuttle 223. It is envisioned that shuttle 223 may be a separate component contained in stapler cartridge 222, or integrally formed on a drive member 250 as seen in FIG. 22.

FIGS. 22-26 sequentially depict actuation of a surgical instrument including the illustrative end effector and reload shown in FIG. 21.

Figure 27:
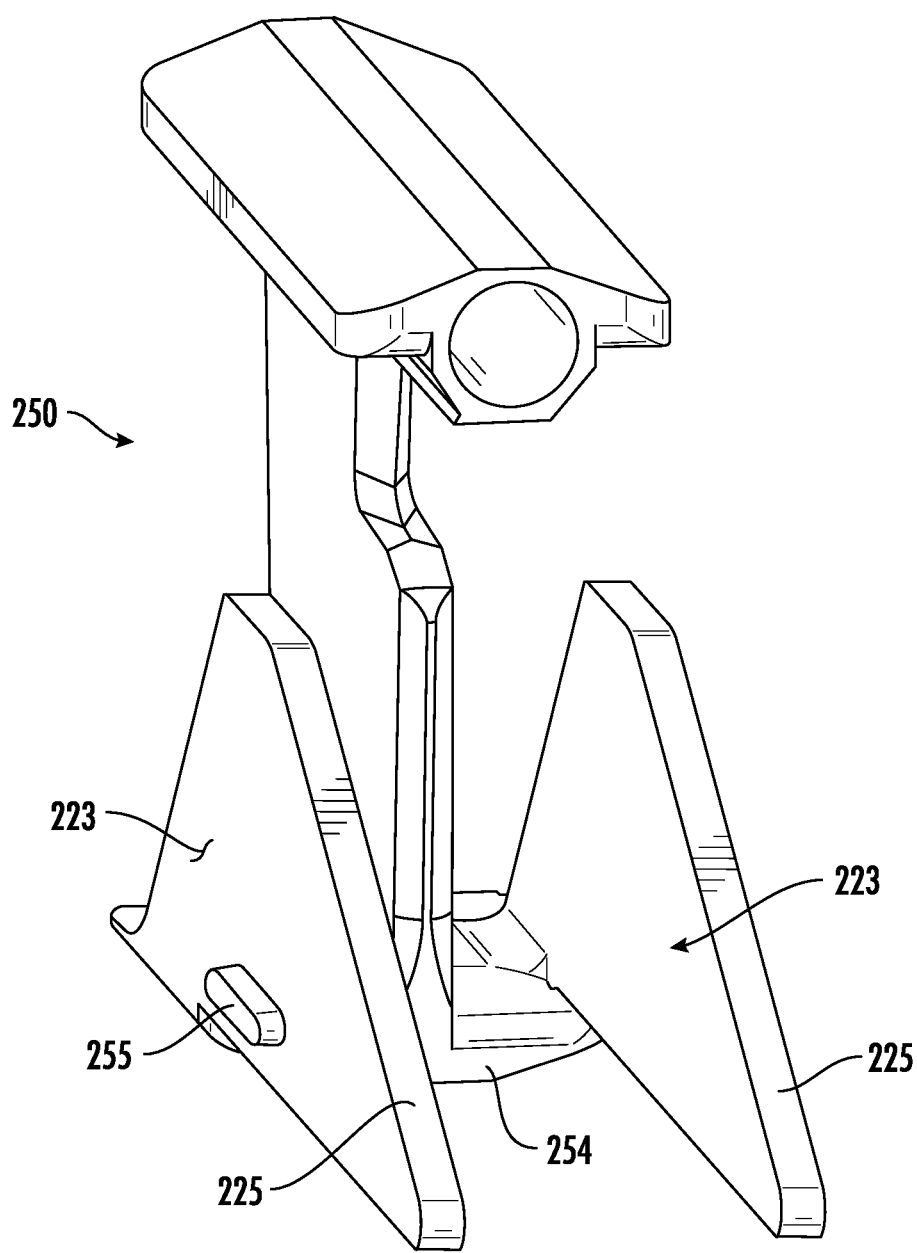
FIG. 27 is a perspective view of an illustrative drive member in accordance with the embodiment of FIG. 16.

In FIG. 22, stapler cartridge 222 includes annular pin 280 in an unraised position corresponding to a freshly installed reload. Upon actuation, a drive member 250 (as shown in FIG. 27) is driven distally through end effector 210. Drive member 250 may have an integrated shuttle component 223 having inclined distal portions 225 attached thereto. In FIG. 23, an inclined distal portion 225 of shuttle 223 engages a lower ramped portion 282 of annular pin 280 applying sufficient force to cause annular pin 280 to be pushed through a cartridge channel 290 towards a raised position.

Figure 24:
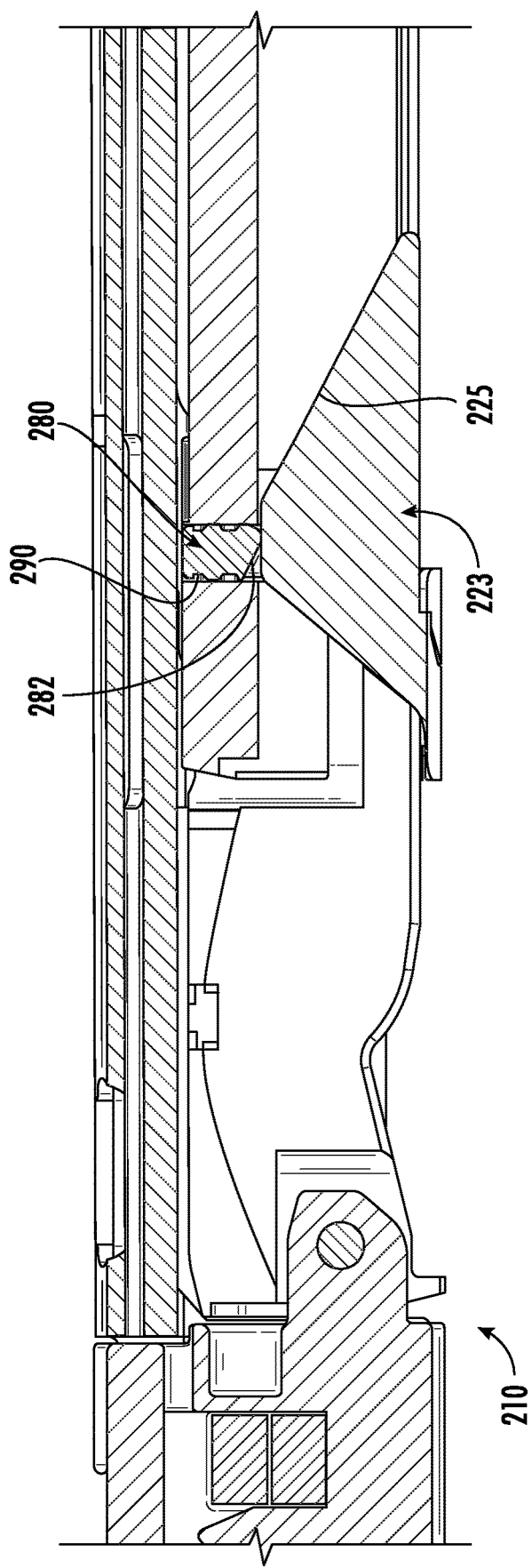
FIG. 24 is a is a partial perspective side view of an illustrative end effector of a surgical instrument having an annular pin in a raised position after engagement with a drive member that has been driven distally.

In FIG. 24, drive member 250 has translated distally such that shuttle 223 has fully engaged and moved annular pin 280 into the raised position. When annular pin 280 is in the raised position, drive member 250 may pass under annular pin 280 to continue to translate distally to sequentially fire staples and cut tissue.

Figure 26:
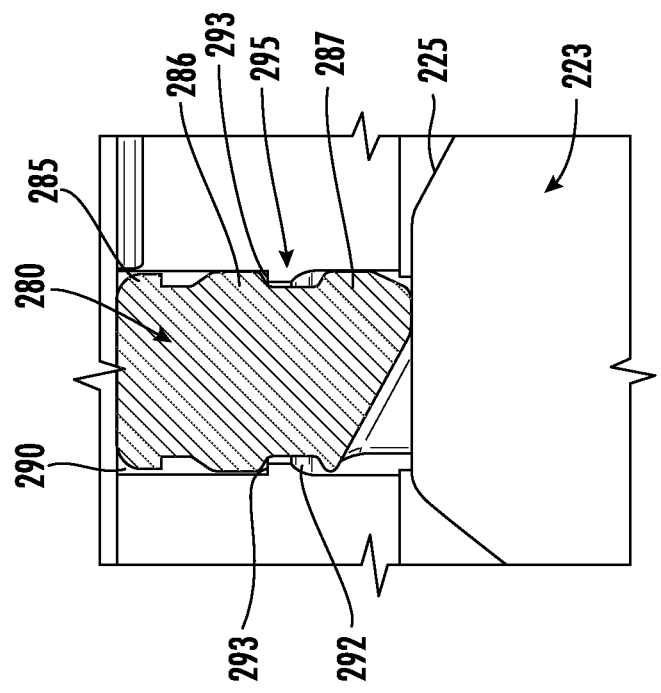
FIG. 26 is an enlarged view of the illustrative embodiment of FIG. 16 showing a drive member that has engaged and moved an annular pin into the raised position.
Figure 25:
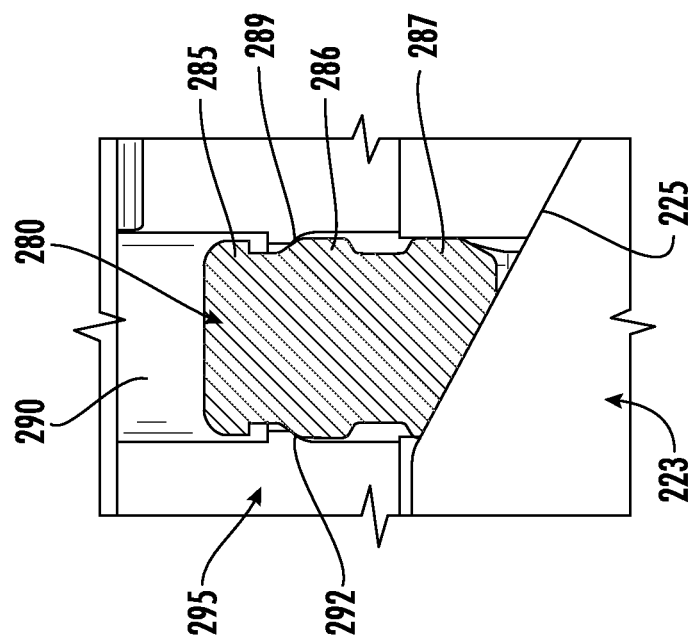
FIG. 25 is an enlarged view of the illustrative embodiment of FIG. 16 showing a drive member engaging an annular pin in an unraised position.

FIGS. 25 and 26 show the mechanism by which annular pin 280 is retained within cartridge 222 once moved into the raised position. Annular pin 280 may have one or more undercuts 284 formed on either side of annular pin 280. In embodiments, annular pin 280 may include an upper undercut 285, a middle undercut 286, and a lower undercut 287. Before being contacted by inclined distal portion 225, annular pin 280 is retained within cartridge channel 290 by engagement of the upper undercut 285 with an upper edge 293 of an interference ring 295 formed within cartridge channel 290. In embodiments, any interferences structure of a suitable shape or size may be used to retain annular pin 280 in channel 290. Channel 281 may include one or more interference rings 295 as desired. In FIG. 20, as inclined distal portion 225 urges annular pin 280 upwards, an amount of force is needed to push middle undercut 286 upward with enough force to be driven past a lower edge 292 of interference ring 295.

In FIG. 26, annular pin 280 has been moved into the raised position in which middle undercut 286 is now above and resting on upper edge 293 of interference ring 295, retaining annular pin 280 within cartridge channel 290 out of the path of shuttle 223 of drive member 250.

Figure 26A:
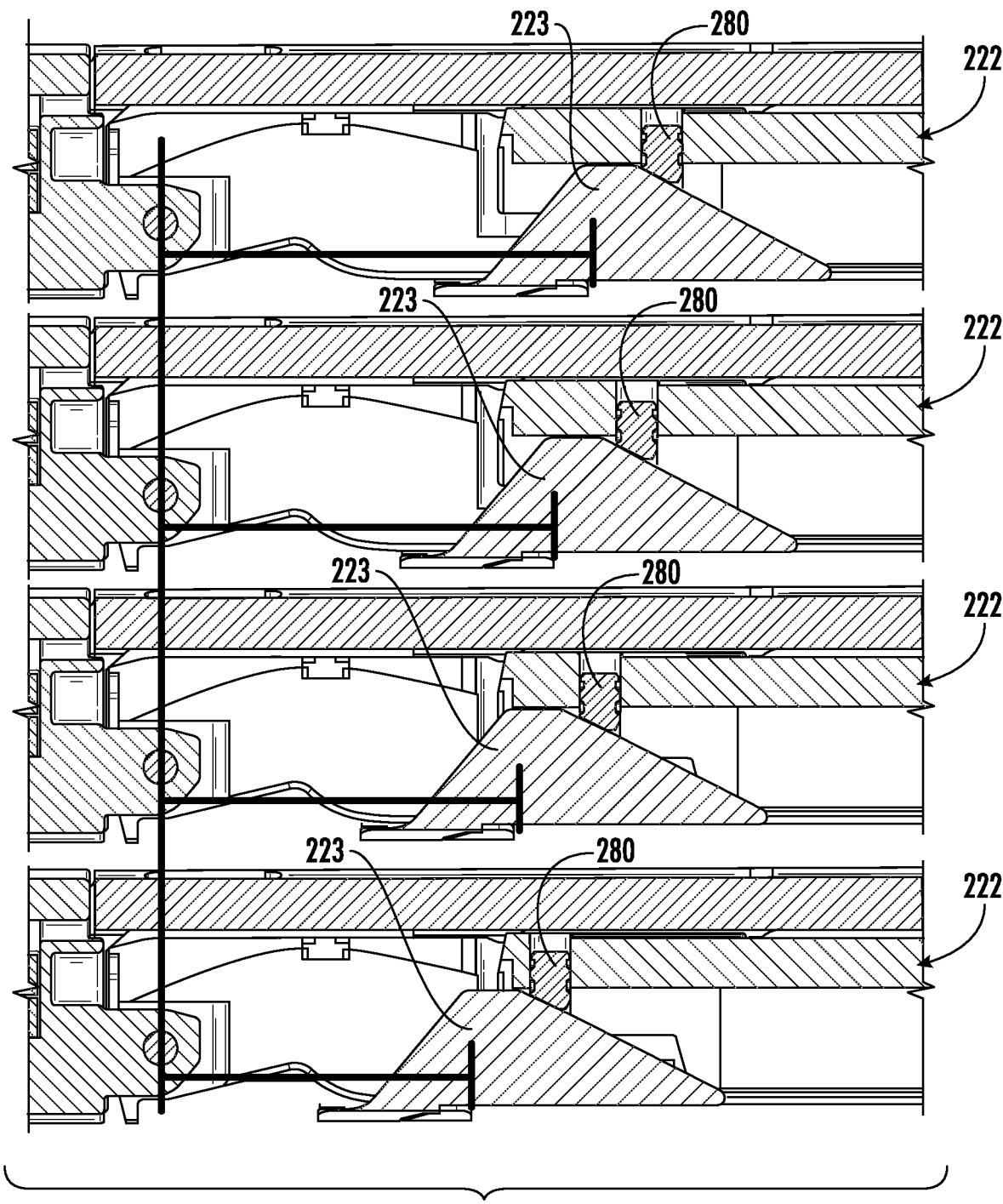
FIG. 26A depicts a partial perspective view of a series of end effectors having installed stapler cartridges including annular pins positioned at a respective axial position within each cartridge.
Figure 28:
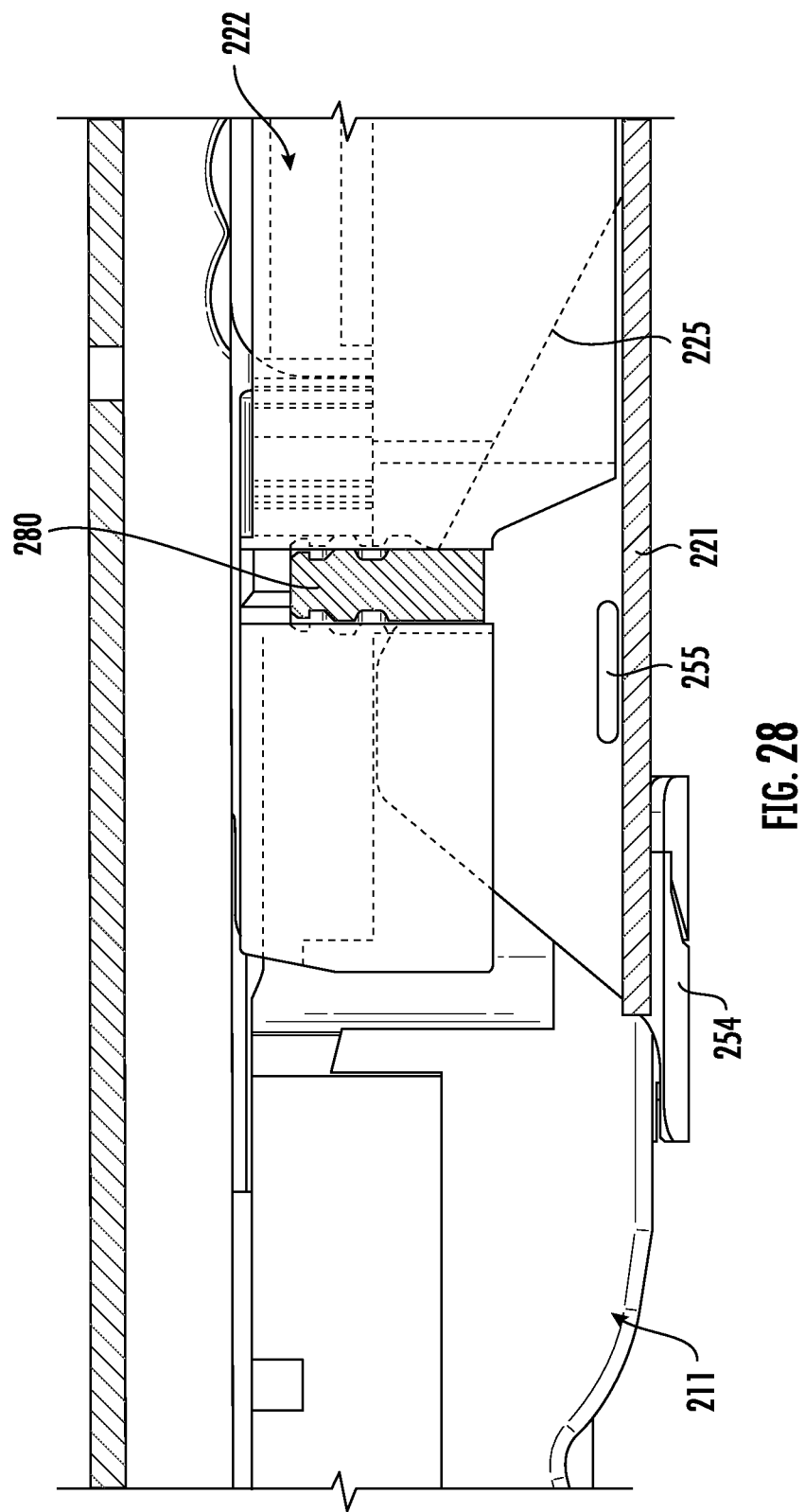
FIG. 28 is a perspective view of the illustrative end effector of FIG. 16 further including an inner wall formed within a channel to help stabilize the drive member upon actuation.

In embodiments, robotic surgical system may be configured to detect the position along a firing stroke at which the inclined distal portion 225 of shuttle 223 engages annular pin 280 via detection of a torque spike, allowing the system to determine the type of reload presently installed. Based on the detected torque spike, a control unit, operatively coupled with the actuation mechanism, may read and process the detectable force to determine the correct amount of force to apply to the drive member in a similar fashion as described above in connection with previously described embodiments. In embodiments, the position of the annular pin and the position of channel 291 and its associated retention features may be moved proximally within different types of reload configured to be installed within cartridge 222 to provide for a unique contact point between annular pin 280 and inclined distal portion 225 as best seen in FIG. 26A. Thus, a surgical system may identify the detectable force at a different axial position along the firing stroke, thus allowing the system to differentiate between different types of reloads installed in a given cartridge 222 based on the position of annular pin 280. It is envisioned that drive member 250 may include any structure capable of engaging annular pin 280 at a given axial position to create a detectable resistance, so long as the accompanying interference structure described above is modified to complement the direction in which annular pin 280 is driven upon engagement by drive member 250. It is also envisioned that an annular pin may engage and maintain a locking member in a disabled position in a similar manner as switch 191 described in connection with previous embodiments in a first position, and may then disengage with the locking member upon actuation to allow the locking member to pivot to a locked position, prevent actuation in the presence of a spent cartridge. FIGS. 27 and 28 illustrate a feature for stabilizing drive member 250 upon actuation of a surgical instrument including an annular pin 280. As inclined distal portion 225 engages annular pin 280 as described above, shuttle 223 and drive member 250 experience a downward force that causes shuttle 223 to deflect away from annular pin 280. When drive member 250 and shuttle 223 experience vertical load, a protrusion 255 formed on shuttle 223 pushes against an inner wall 221 formed within a channel of jaw member 211 (above lower shoe 254) providing a counter force. Inner wall 221 and the counter force it provides reduces the deflection of shuttle 223 and drive member 250, ensuring more controlled engagement between annular pin 280 and shuttle 223 and limiting potential stress or damage to drive member 250 from excessive deflection or bending.

Figure 29:
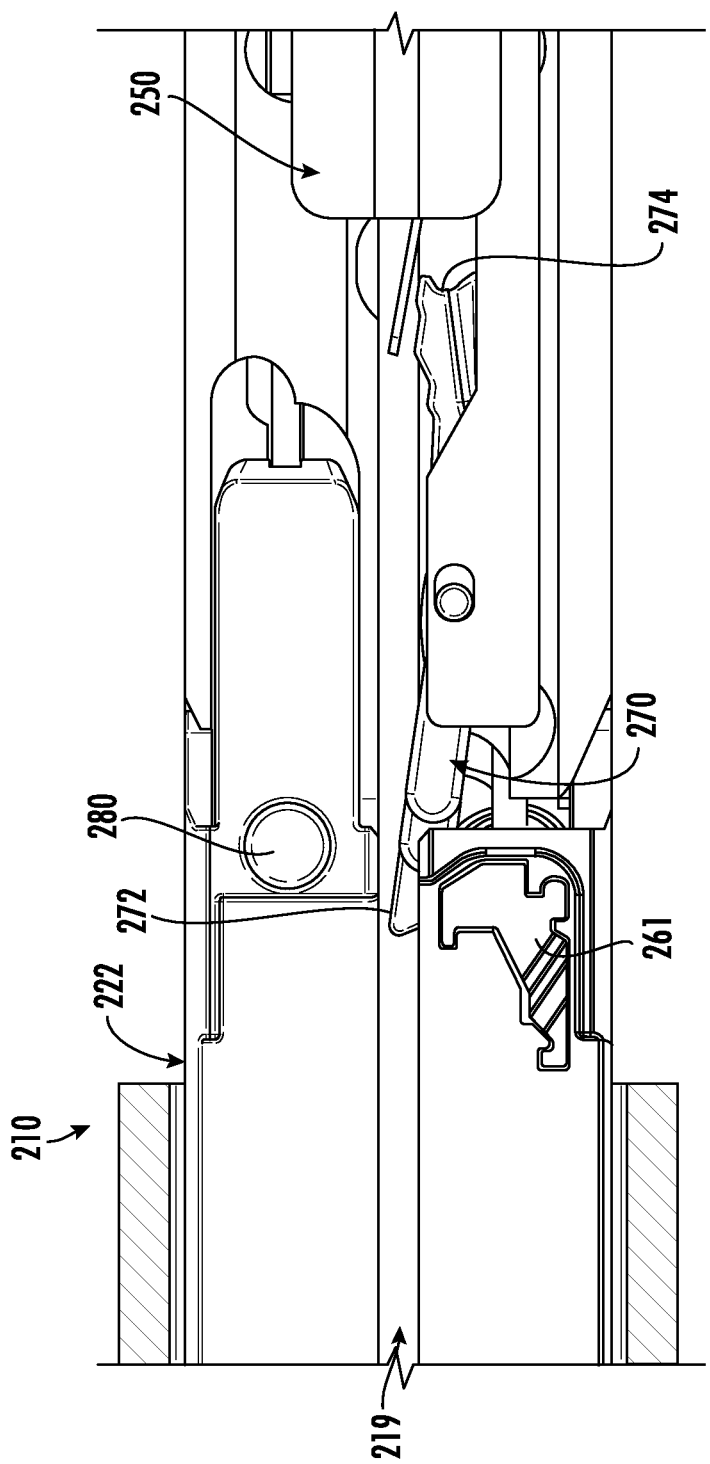
FIG. 29 a partial perspective top view of an illustrative end effector of a surgical instrument having an annular pin and a switch-activated locking mechanism in an unlocked position.
Figure 30:
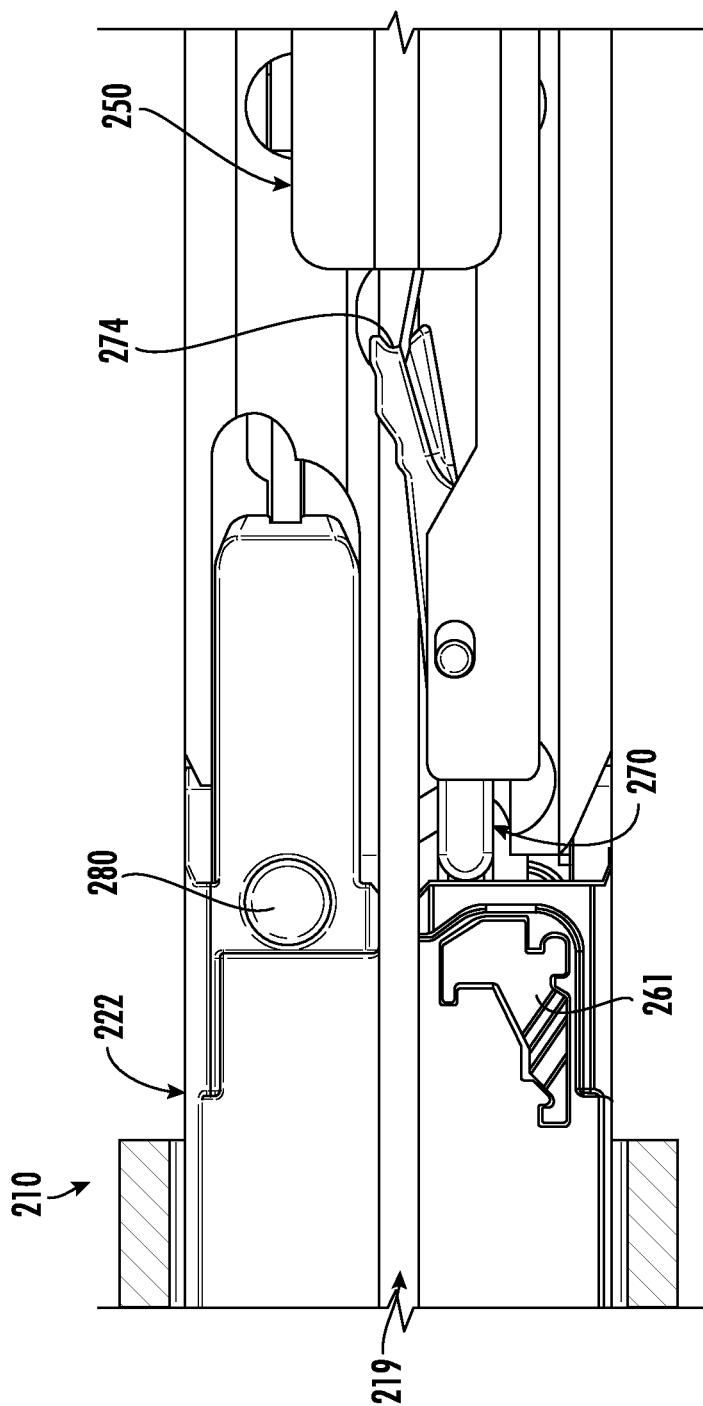
FIG. 30 a partial perspective top view of an illustrative end effector of a surgical instrument having an annular pin and a switch-activated locking mechanism in a locked position.

In embodiments, an illustrative end effector 210 may include both an annular pin 280 for reload detection, and a switch 261 for engaging a locking member 270. In FIGS. 29 and 30, an illustrative end effector 210 including an annular pin 280 on one side of a stapler cartridge 222, and a switch 261 on the opposing side of stapler cartridge 222. Annular pin 280 functions as described above in connection with FIGS. 24-26. In FIG. 29, a locking member 270 includes an engagement portion 274 that is being held out of channel 219 through which drive member 250 travels distally. A spring 278 biases locking member 270 towards channel 219, however, switch 261 engages a distal portion 272 of locking member 270, retaining the proximal engagement portion out of alignment with channel 219. FIG. 30 depicts locking member 270 with engagement portion 274 protruding into channel 219 to obstruct drive member 250 after actuation of the instrument. Switch 261 has been moved into a raised position, and distal portion 272 of locking member has now moved out of channel 219 towards a position below switch 261, thereby causing engagement portion 274 to translate towards channel 219. In this configuration, an attempt to actuate the instrument again would cause drive member 250 to be obstructed by engagement portion 274 of lock 270.

Figure 31:
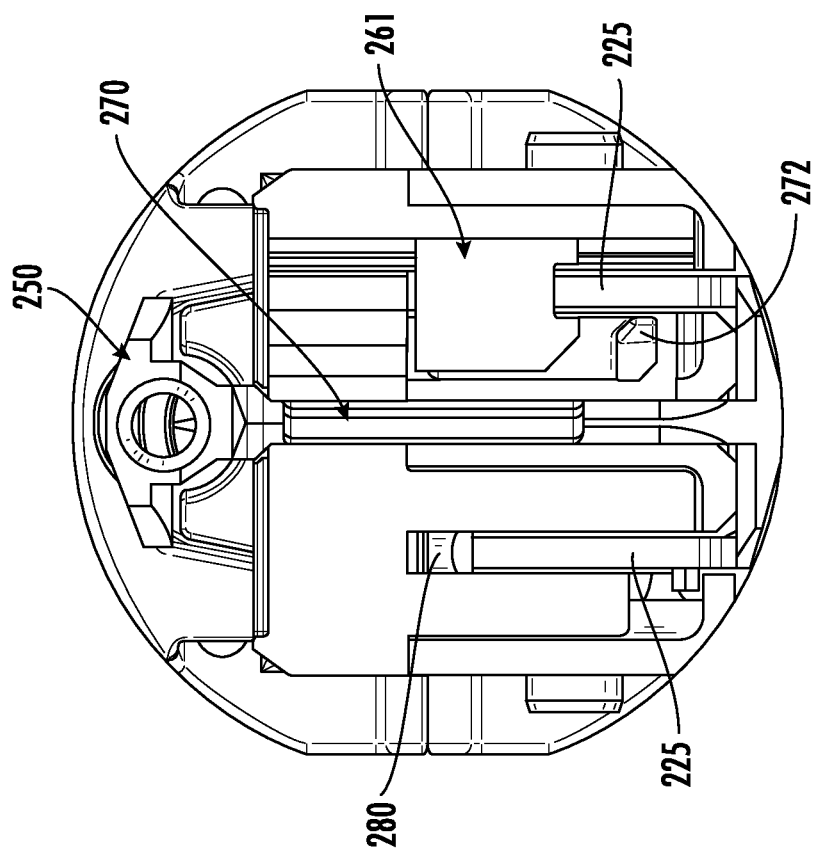
FIG. 31 is a cross-sectional view of an illustrative end effector of a surgical instrument having an annular pin and a switch-activated locking mechanism in the unlocked position.
Figure 32:
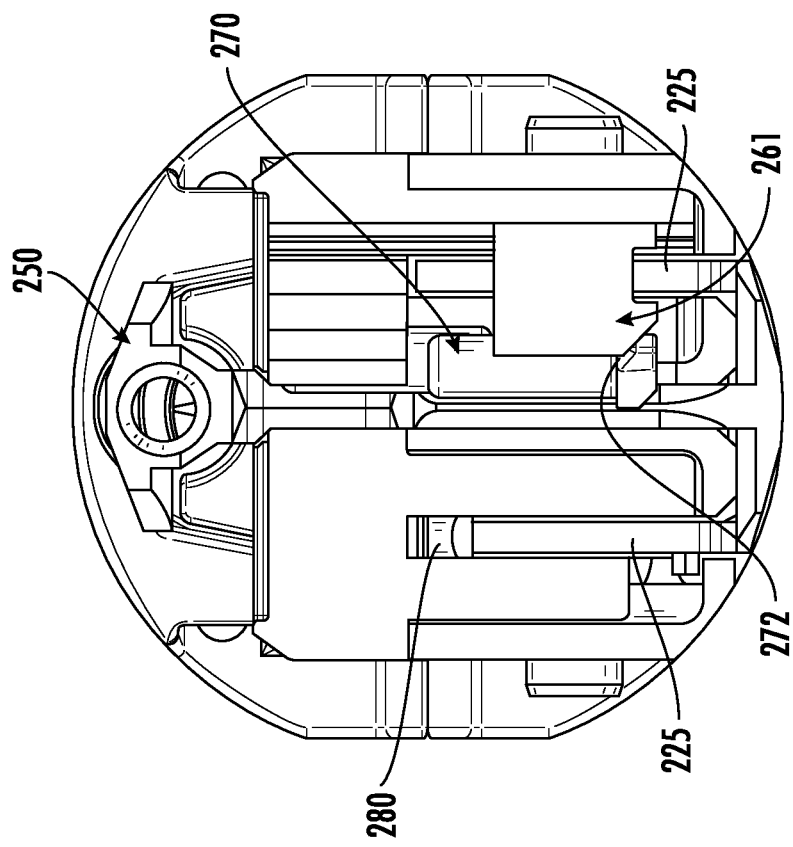
FIG. 32 is a cross-sectional view of an illustrative end effector of a surgical instrument having an annular pin and a switch-activated locking mechanism in the locked position.

FIGS. 31 and 32 show cross sectional views depicting actuation within the end effector of FIGS. 29 and 30.

In FIG. 31, drive member 250 is able to translate through channel 219 (as seen in FIG. 30) unobstructed, as locking member 270 is being held out of engagement with channel 219 by switch 261 as it sits in the unraised position. FIG. 31 further shows inclined distal portion 225 aligned with, and about to engage, a cutout 262 formed on switch 261. In FIG. 32, switch 261 has been driven to the raised position, allowing distal portion 272 of locking member 270 to swing underneath switch 261, causing the proximal engagement portion 274 of locking member 270 to swing in an opposing direction towards channel 219. Should a user retract drive member 250 and attempt to actuate the surgical instrument, engagement portion 274 (now aligned with drive member 250 within channel 219) of locking member 270 would obstruct drive member 250 and prevent cutting of tissue or firing of staples.

In embodiments, surgical instruments in accordance with this disclosure may alternatively include switches configured to be sheared along an axis, or switches having vertical cutouts designed to be engaged by an inclined distal portion of a drive member for purposes of engaging a lockout assembly, providing for reload recognition, or both, as described in U.S. Provisional Application No. 62/783,429, the entire disclosure of which is incorporated herein by reference.

Figure 33:
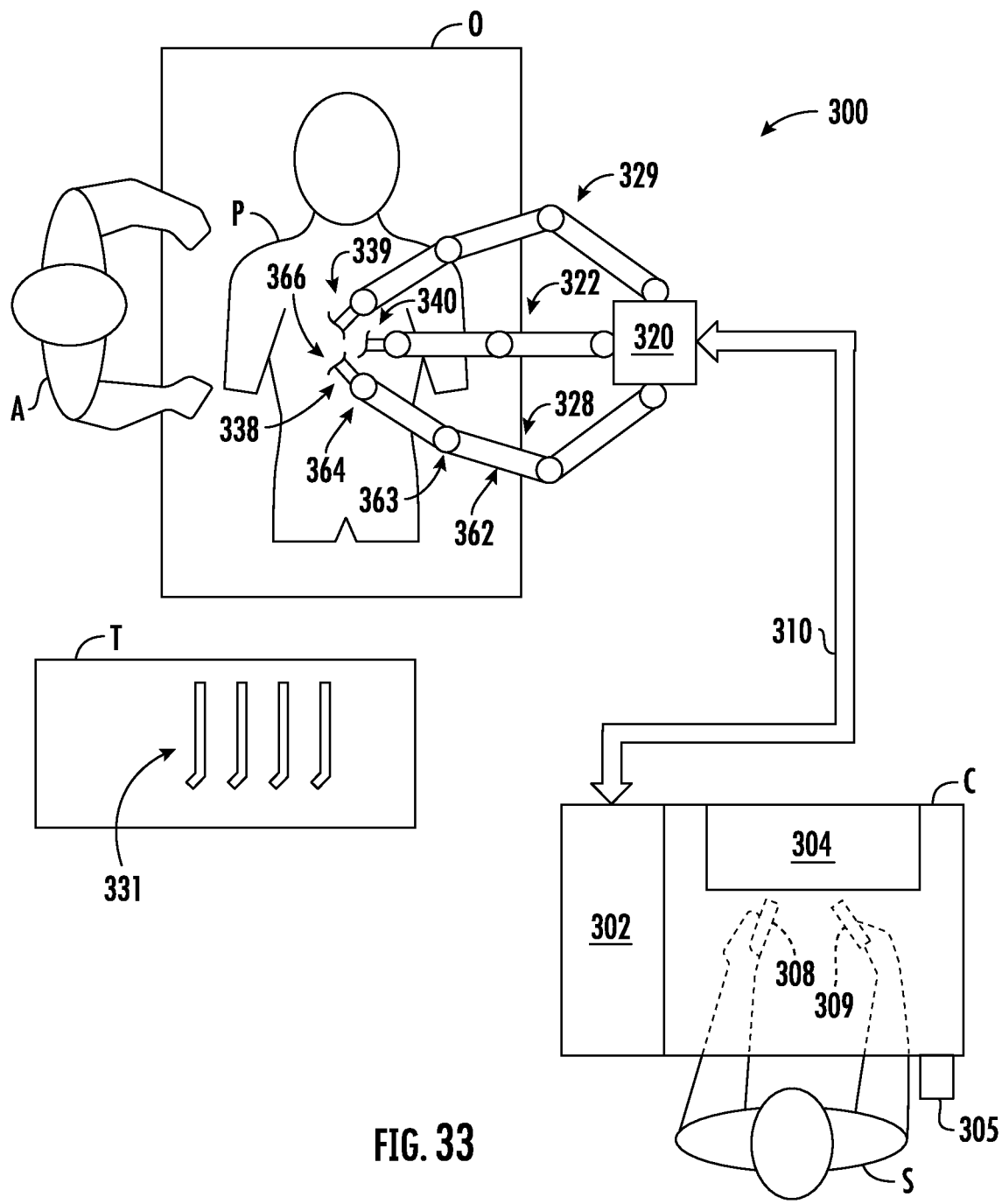
FIG. 33 illustrates a top view of an operating room employing a robotic surgical system utilizing aspects of the present disclosure.

FIG. 33 illustrates, as an example, a top view of an operating room employing a robotic surgical system. The robotic surgical system in this case is a robotic surgical system 300 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a monitor 304 for displaying an image of a surgical site to the Surgeon, left and right manipulatable control devices 308 and 309, a foot pedal 305, and a processor 302. The control devices 308 and 309 may include any one or more of a variety of input devices such as joysticks, gloves, trigger-guns, hand-operated controllers, or the like. The processor 302 may be a dedicated computer that may be integrated into the Console or positioned next to it.

The Surgeon performs a minimally invasive surgical procedure by manipulating the control devices 308 and 309 (also referred to herein as "master manipulators") so that the processor 302 causes their respectively associated robotic arm assemblies, 328 and 329, (also referred to herein as "slave manipulators") to manipulate their respective removably coupled surgical instruments 338 and 339 (also referred to herein as "tools") accordingly, while the Surgeon views the surgical site in 3-D on the Console monitor 304 as it is captured by a stereoscopic endoscope 340.

Each of the tools 338 and 339, as well as the endoscope 340, may be inserted through a cannula or other tool guide (not shown) into the Patient so as to extend down to the surgical site through a corresponding minimally invasive incision such as incision 366. Each of the robotic arms is conventionally formed of links, such as link 362, which are coupled together and manipulated through motor controlled or active joints, such as joint 363.

The number of surgical tools used at one time and consequently, the number of robotic arms being used in the system 300 will generally depend on the diagnostic or surgical procedure and the space constraints within the operating room, among other factors. If it is necessary to change one or more of the tools being used during a procedure, the Assistant may remove the tool no longer being used from its robotic arm, and replace it with another tool 331 from a Tray ("T") in the operating room.

The monitor 304 may be positioned near the Surgeon's hands so that it will display a projected image that is oriented so that the Surgeon feels that he or she is actually looking directly down onto the operating site. To that end, images of the tools 338 and 339 may appear to be located substantially where the Surgeon's hands are located.

The processor 302 performs various functions in the system 300. One function that it performs is to translate and transfer the mechanical motion of control devices 308 and 309 to their respective robotic arms 328 and 329 through control signals over bus 310 so that the Surgeon can effectively manipulate their respective tools 338 and 339. Another important function is to implement various control system processes as described herein.

Although described as a processor, it is to be appreciated that the processor 302 may be implemented in practice by any combination of hardware, software and firmware. Also, its functions as described herein may be performed by one unit, or divided up among different components, each of which may be implemented in turn by any combination of hardware, software and firmware.

For additional details on robotic surgical systems, see, e.g., commonly owned U.S. Pat. Nos. 6,493,608, 6,671, and International Application WO 2017/132611. Each of these disclosures is herein incorporated in its entirety by this reference.

Figure 34:
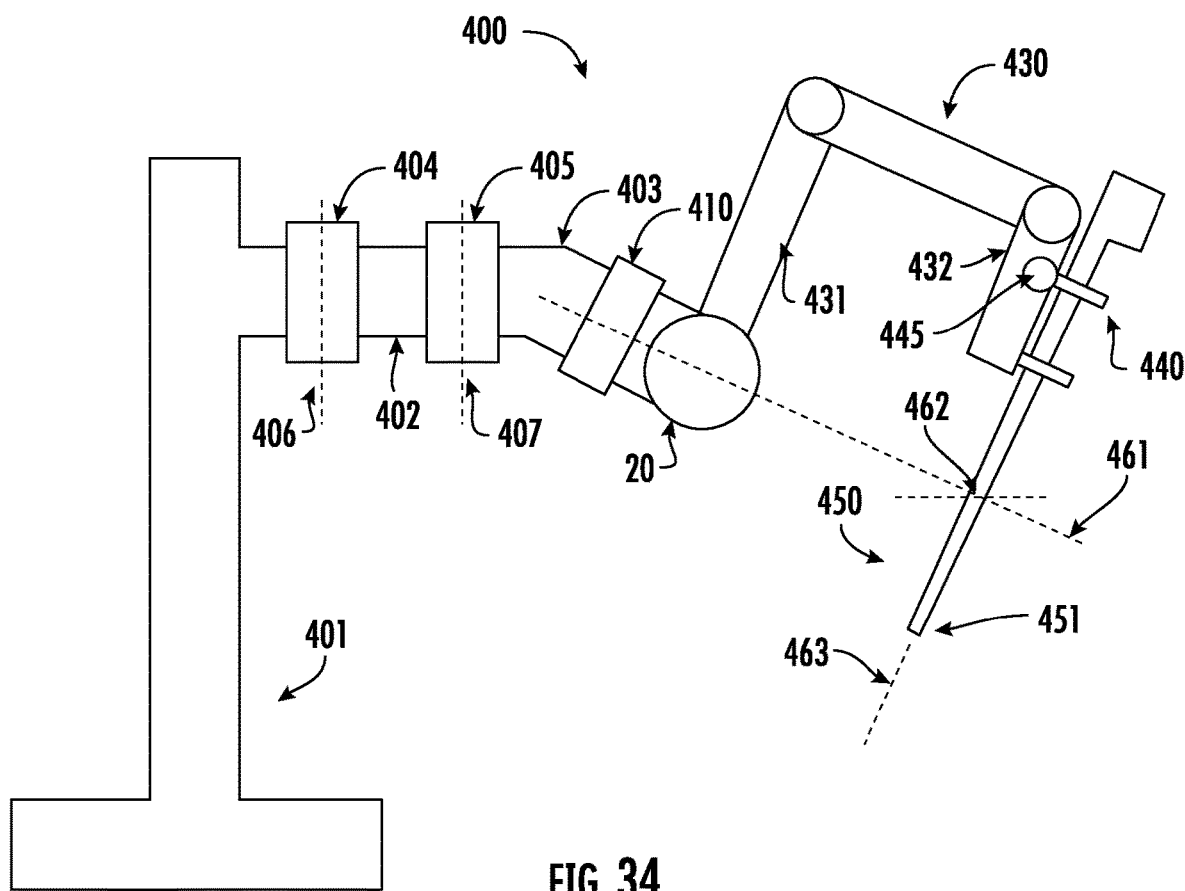
FIG. 34 illustrates a simplified side view of a robotic arm assembly that is usable with various aspects of the present disclosure.

FIG. 34 illustrates, as an example, a side view of a simplified (not necessarily in proportion or complete) illustrative robotic arm assembly 400 (which is representative of robotic arm assemblies 328 and 329) holding a surgical instrument 450 (which is representative of tools 338 and 339) for performing a surgical procedure. The surgical instrument 450 is removably held in tool holder 440. The arm assembly 400 is mechanically supported by a base 401, which may be part of a patient-side movable cart or affixed to the operating table or ceiling. It includes links 402 and 403 which are coupled together and to the base 401 through setup joints 404 and 405.

The setup joints 404 and 405 in this example are passive joints that allow manual positioning of the arm 400 when their brakes are released. For example, setup joint 404 allows link 402 to be manually rotated about axis 406, and setup joint 405 allows link 403 to be manually rotated about axis 407.

Although only two links and two setup joints are shown in this example, more or less of each may be used as appropriate in this and other robotic arm assemblies in conjunction with the present disclosure. For example, although setup joints 404 and 405 are useful for horizontal positioning of the arm 400, additional setup joints may be included and useful for limited vertical and angular positioning of the arm 400. For major vertical positioning of the arm 400, however, the arm 400 may also be slidably moved along the vertical axis of the base 401 and locked in position.

The robotic arm assembly 400 also includes three active joints driven by motors. A yaw joint 410 allows arm section 430 to rotate around an axis 461, and a pitch joint 420 allows arm section 430 to rotate about an axis perpendicular to that of axis 461 and orthogonal to the plane of the drawing. The arm section 430 is configured so that sections 431 and 432 are always parallel to each other as the pitch joint 420 is rotated by its motor. As a consequence, the instrument 450 may be controllably moved by driving the yaw and pitch motors so as to pivot about the pivot point 462, which is generally located through manual positioning of the setup joints 404 and 405 so as to be at the point of incision into the patient. In addition, an insertion gear 445 may be coupled to a linear drive mechanism (not shown) to extend or retract the instrument 450 along its axis 463.

Although each of the yaw, pitch and insertion joints or gears, 410, 420 and 445, is controlled by an individual joint or gear controller, the three controllers are controlled by a common master/slave control system so that the robotic arm assembly 400 (also referred to herein as a "slave manipulator") may be controlled through user (e.g., surgeon) manipulation of its associated master manipulator.

While several embodiments have been shown in the drawings, it is not intended that the disclosure be limited thereto, as it is intended that the disclosure be as broad in scope as the art will allow and that the specification be read likewise. For example, the invention is not limited to the mechanisms described herein for identifying and/or deactivating stapler cartridges. Other suitable devices or mechanisms are described in co-pending and co-owned International Patent Application No. PCT/US19/66513, filed Dec. 16, 2019 and entitled "SURGICAL INSTRUMENTS WITH SWITCHES FOR DEACTIVATING AND/OR IDENTIFYING STAPLER CARTRIDGES", the complete disclosure of which is herein incorporated by reference in its entirety for all purposes. Therefore, the above description should not be construed as limiting, but merely as exemplifications of presently disclosed embodiments. Thus, the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical stapling instrument comprising:
    an end effector defining a longitudinal axis including a first jaw and a second jaw, the first jaw including an anvil and, the second jaw configured to receive a stapler cartridge having one or more staples and a switch movably coupled to the stapler cartridge;
    a drive member configured to translate distally through the end effector;
    a staple cartridge;
    a locking member movable from a disabled position permitting distal translation of the drive member to at least an axial position wherein the drive member engages at least one of the staples, to a locking position inhibiting distal translation of the drive member to said axial position; and
    wherein the locking member is configured to move between the disabled and locking positions based on a lateral position of the switch;
    wherein the switch is positioned within a slot formed on a tail portion of the staple cartridge and wherein the switch is movable in a lateral direction relative to the longitudinal axis, from a first position wherein the switch maintains the locking member in the disabled position to a second position wherein the switch disengages the locking member, wherein the slot includes one or more detents formed therein, the detents being configured to provide mechanical resistance when the drive member engages the switch.

2. The surgical stapling instrument of claim 1, wherein the locking member is movable in a first lateral direction substantially perpendicular to the longitudinal axis from the disabled position to the locking position.

3. The surgical stapling instrument of claim 1, wherein the locking member pivots between the disabled position and the locking position about a pivot point that is laterally offset from the longitudinal axis of the end effector.

4. The surgical stapling instrument of claim 3, wherein the locking member pivots in a direction substantially perpendicular to the longitudinal axis defined by the end effector.

5. The surgical stapling instrument of claim 1, wherein the locking member is biased towards the locking position.

6. The surgical stapling instrument of claim 1, wherein the locking member includes a switch contacting portion and a proximal engagement portion positioned to obstruct the drive member from moving distally when the locking member is in the second position.

7. The surgical stapling instrument of claim 1, wherein the drive member includes an inclined surface, and a chamfered surface, wherein upon distal advancement of the drive member, the chamfered surface of the drive member engages a chamfered surface of the switch while the switch is in the first position.

8. The surgical stapling instrument according to claim 1 further comprising an actuation mechanism configured to translate the drive member distally through the end effector, wherein the actuation mechanism includes a coil that applies a distal force to the drive member.

9. The surgical stapling instrument according to claim 8, further comprising an actuator operatively connected to the actuation mechanism, wherein the actuator includes a control device of a robotic surgical system.

10. A surgical stapling instrument comprising:
    a stapler cartridge comprising a switch movably coupled to the stapler cartridge;
    an end effector defining a longitudinal axis including a first jaw and a second jaw, the first jaw including an anvil and, the second jaw configured to receive the stapler cartridge;
    a drive member configured to translate distally through the end effector;
    wherein the drive member is configured to contact the switch at an axial position of the drive member relative to the end effector, and wherein the switch is configured to provide a detectable resistance upon engagement of the drive member at said axial position; and
    wherein the switch is positioned within a slot formed on a tail portion of the stapler cartridge, wherein the slot formed on the tail portion of the cartridge includes one or more detents formed therein, the detents configured to provide mechanical resistance when the drive member engages the switch.

11. The surgical instrument of claim 10, wherein the surgical instrument is operatively coupled to a control unit, the control unit configured to process the detectable resistance to identify the stapler cartridge.

12. The surgical instrument of claim 11, further including a locking member, wherein the switch is movable in a first lateral direction substantially perpendicular to the longitudinal axis, from a first position wherein the switch maintains the locking member in a disabled position to a second position wherein the switch disengages from the locking member.

13. The surgical instrument of claim 12 further comprising an actuation mechanism configured to translate the drive member distally through the end effector, wherein the actuation mechanism includes a coil that applies a distal force to the first portion of the drive member.

14. The surgical stapling instrument according to claim 13, further comprising an actuator operatively connected to the actuation mechanism, wherein the actuator includes a control device of a robotic surgical system.

15. The surgical stapling instrument according to claim 10, wherein the switch comprises an annular pin positioned within a channel formed in the stapler cartridge, the annular pin movable from an unraised position to a second raised position within the channel formed in the stapler cartridge.

16. The surgical instrument according to claim 15, wherein the channel formed in the staple cartridge includes at least one interference structure formed therein, the interference structure configured to retain the annular pin within the channel formed in the staple cartridge.

17. The surgical instrument according to claim 16, wherein the annular pin includes one or more undercuts formed thereon to engage with the interference structure to retain the annular pin within the channel formed in the staple cartridge.

18. A surgical stapling instrument comprising:
a stapler cartridge comprising a switch movably coupled to the stapler cartridge;
an end effector defining a longitudinal axis including a first jaw and a second jaw, the first jaw including an anvil and, the second jaw configured to receive the stapler cartridge;
a drive member configured to translate distally through the end effector;
wherein the drive member is configured to contact the switch at an axial position of the drive member relative to the end effector, and wherein the switch is configured to provide a detectable resistance upon engagement of the drive member at said axial position; and
a locking member, wherein the switch is movable in a first lateral direction substantially perpendicular to the longitudinal axis, from a first position wherein the switch maintains the locking member in a disabled position to a second position wherein the switch disengages from the locking member, wherein the surgical stapling instrument is operatively coupled to a control unit, the control unit configured to process the detectable resistance to identify the stapler cartridge.

19. A surgical stapling instrument comprising:
a stapler cartridge comprising a switch movably coupled to the stapler cartridge;
an end effector defining a longitudinal axis including a first jaw and a second jaw, the first jaw including an anvil and, the second jaw configured to receive the stapler cartridge;
a drive member configured to translate distally through the end effector;
wherein the drive member is configured to contact the switch at an axial position of the drive member relative to the end effector, and wherein the switch is configured to provide a detectable resistance upon engagement of the drive member at said axial position; and
wherein the switch comprises an annular pin positioned within a channel formed in the stapler cartridge, the annular pin movable from an unraised position to a second raised position within the channel formed in the stapler cartridge.

* * * * *